(12) United States Patent
Ben-Ezra et al.

(10) Patent No.: US 7,929,142 B2
(45) Date of Patent: Apr. 19, 2011

(54) PHOTODIODE-BASED BI-DIRECTIONAL REFLECTANCE DISTRIBUTION FUNCTION (BRDF) MEASUREMENT

(75) Inventors: Moshe Ben-Ezra, Beijing (CN); Yasuyuki Matsushita, Beijing (CN); Bennett S Wilburn, Beijing (CN); Xiaoyang Li, Ithaca, NY (US)

(73) Assignee: Microsoft Corporation, Redmond, WA (US)

( * ) Notice: Subject to any disclaimer, the term of this patent is extended or adjusted under 35 U.S.C. 154(b) by 207 days.

(21) Appl. No.: 12/173,655

(22) Filed: Jul. 15, 2008

(65) Prior Publication Data

US 2009/0079987 A1 Mar. 26, 2009

Related U.S. Application Data

(60) Provisional application No. 60/975,059, filed on Sep. 25, 2007.

(51) Int. Cl.
G01N 21/55 (2006.01)
(52) U.S. Cl. ....................................................... 356/445
(58) Field of Classification Search .................... 356/445
See application file for complete search history.

(56) References Cited

U.S. PATENT DOCUMENTS

| | | | | |
|---|---|---|---|---|
| 3,947,127 A | * | 3/1976 | Bennett et al. | 356/124 |
| 4,311,393 A | * | 1/1982 | Bartke | 356/407 |
| 4,368,983 A | * | 1/1983 | Bennett | 356/445 |
| 4,770,536 A | * | 9/1988 | Golberstein | 356/600 |
| 4,914,309 A | * | 4/1990 | Masaharu et al. | 250/559.48 |
| 4,917,500 A | * | 4/1990 | Lugos | 356/406 |
| 5,196,906 A | | 3/1993 | Stover et al. | |
| 5,313,542 A | * | 5/1994 | Castonguay | 385/115 |
| 5,475,617 A | * | 12/1995 | Castonguay | 382/254 |
| 5,615,294 A | * | 3/1997 | Castonguay | 385/115 |
| 5,640,246 A | * | 6/1997 | Castonguay | 356/445 |
| 6,172,745 B1 | * | 1/2001 | Voser et al. | 356/71 |
| 6,765,573 B2 | | 7/2004 | Kouadio | |
| 6,903,813 B2 | * | 6/2005 | Jung et al. | 356/73 |
| 6,921,898 B1 | | 7/2005 | Chen | |
| 6,982,794 B1 | | 1/2006 | Davis et al. | |
| 6,987,568 B2 | | 1/2006 | Dana | |
| 7,075,534 B2 | | 7/2006 | Cole et al. | |
| 7,079,137 B2 | | 7/2006 | Borshukov | |
| 7,095,502 B2 | * | 8/2006 | Lakowicz et al. | 356/445 |
| 7,190,461 B2 | | 3/2007 | Han et al. | |
| 7,221,455 B2 | * | 5/2007 | Chediak et al. | 356/419 |
| 7,557,924 B2 | * | 7/2009 | Nisper et al. | 356/419 |
| 7,626,709 B2 | * | 12/2009 | Schwarz et al. | 356/600 |
| 2005/0018195 A1 | * | 1/2005 | Lex | 356/445 |
| 2005/0157301 A1 | * | 7/2005 | Chediak et al. | 356/417 |
| 2005/0276441 A1 | | 12/2005 | Debevec | |
| 2006/0033922 A1 | * | 2/2006 | Sperling et al. | 356/446 |

(Continued)

OTHER PUBLICATIONS

Coburn, et al., "A Low-Cost Field and Laboratory Goniometer System for Estimating Hyperspectral Bidirectional Reflectance", CASI, vol. 32, No. 3, 2006, pp. 244-253.

(Continued)

*Primary Examiner* — Roy Punnoose
(74) *Attorney, Agent, or Firm* — Lee & Hayes, PLLC

(57) ABSTRACT

Photodiode-based bi-directional reflectance distribution function (BRDF) measurement is described. Multiple photodiodes are distributed approximately symmetrically at a fixed distance from a surface to be measured. One or more of the photodiodes are directed to emit light, while readings are gathered from the other photodiodes that are not emitting light. The readings are processed based on previously measured calibration data to generate BRDF values.

18 Claims, 22 Drawing Sheets

U.S. PATENT DOCUMENTS

| | | |
|---|---|---|
| 2006/0227137 A1 | 10/2006 | Weyrich et al. |
| 2006/0245632 A1 | 11/2006 | Nisper et al. |
| 2007/0035740 A1* | 2/2007 | Nisper et al. .................. 356/446 |
| 2007/0216905 A1 | 9/2007 | Han et al. |
| 2007/0268366 A1 | 11/2007 | Raskar et al. |

OTHER PUBLICATIONS

Falke, et al., "Led in-flight calibration and model-based development of ACS algorithm for the university micro-satellite flying laptop", available at least as early as May 22, 2007, at <<http://www.irs.uni-stuttgart.de/institut/mitarbeiter/falke/4S-Symposium2006_Model-based-ACS-algorithm-Development.pdf>, pp. 9.

Giardino, et al.,, "The application of a dedicated device to acquire bidirectional reflectance factors over natural surfaces", available at least as early as May 22, 2007, at <<http://milano.irea.cnr.it/calval/mandrons/print_brdf.pdf>>, Taylor & Francis Ltd, vol. 24, No. 14, 2003, pp. 2989-2995.

Irani, et al., "Improving Resolution by Image Registration", Graphical Models and Image Processing, vol. 53, No. 3 May 1991, pp. 231-239.

Marschner, et al., "Image-Based BRDF Measurement Including Human Skin", pp. 1-15.

McGuckin, et al., "Directional Reflectance Characterization Facility and Measurement Methodology", pp. 1-26.

Schechner, et al., "A Theory of Multiplexed Illumination", IEEE, 2003, pp. 1-8.

Shell II, et al., "A Novel Brdf Measurement Technique With Spatial Resolution-Dependent Spectral Variance", pp. 1-4.

Ward, "Measuring and Modeling Anistropic Reflection", ACM, 1992, pp. 265-272.

* cited by examiner

US 7,929,142 B2

PHOTODIODE-BASED BI-DIRECTIONAL REFLECTANCE DISTRIBUTION FUNCTION (BRDF) MEASUREMENT

RELATED APPLICATIONS

This application claims priority to U.S. Provisional Patent Application Ser. No. 60/975,059, entitled "Photodiode-Based Bi-Directional Distribution Function (BRDF) Measurement" filed Sep. 25, 2007, to Ben-Ezra et al., the disclosure of which is incorporated by reference herein.

SUMMARY

Photodiode-based bi-directional reflectance distribution function (BRDF) measurement is described herein. In an exemplary implementation, multiple photodiodes are directed toward a surface to be measured. One or more of the photodiodes emit light, while reflection readings are obtained from other photodiodes. Each one of the photodiodes can, at any particular time, act as either a light source or a light detector. In an implementation, each of the photodiodes is a light emitting diode (LED).

BACKGROUND

Measuring and predicting the appearance of objects under different illumination and viewing conditions is critical for many applications in computer graphics and computer vision. An important component of appearance information is the Bi-Directional Reflectance Distribution Function (BRDF), which is used to describe geometrical reflectance properties of a surface. The BRDF is defined as the ratio of reflected radiance exiting from a surface in a particular direction $\Omega_e = (\theta_e, \phi_e)$, to the irradiance incident on the surface from direction $\Omega_i = (\theta_i, \phi_i)$, for a particular wavelength $\lambda$, and may be written as $f_r(\Omega_i, \Omega_e, \lambda) = (dL(\Omega_e, \lambda))/(dE(\Omega_i, \lambda))$.

BRDF capture, and in particular, fast acquisition of high-resolution BRDF values is challenging. The BRDF is often dependent on light wavelength and structural and optical properties of the surface being measured, such as light scattering, shadowing, light transmission, reflection, absorption, and emission by surface elements and facets. BRDF is usually integrated across a small patch, such that micro-texture is embedded within the BRDF, but not global orientation.

Most existing BRDF capture methods require a large, sophisticated setup with a camera and mirrors, and some also suffer from occlusions. Some methods require specially shaped material samples, while others require that the sample be placed inside the measurement device. Such systems cannot be used easily outside of a lab for data acquisition in the field. Furthermore, because the dynamic range of BRDFs is typically quite large, projector-camera systems must take multiple exposures in order to capture high dynamic rate measurements, limiting their maximum measurement rates.

FIG. 1 shows a gonioreflectometer 100, which is a conventional device used to capture BRDF values by moving the light source 102, the camera 104, and the object 106. The gonioreflectometer 100 is cumbersome, and since it only measures one point at a time, it takes a long time to capture the full range of the BRDF.

FIGS. 2 and 3 illustrate two examples of alternate techniques for capturing BRDF values. It is recognized that many other techniques may also be used, and those illustrated are merely representative examples.

FIG. 2 illustrates an alternate technique, known as the "Ward technique", for capturing BRDF. The "Ward technique" 200 uses a mirror 202 and a camera 204 to capture multiple views of the sample object 206 in parallel (and in one case, to also reflect the light 208 from different directions).

FIG. 3 illustrates another alternate technique, known as the "Marschner technique", for capturing BRDF. The "Marschner technique" 300 uses a specially formed homogeneous sample 302 to capture different orientations. The techniques illustrated in FIG. 2 and FIG. 3 could conceivably be combined if the sample is shaped as a sphere and is of a homogeneous material.

While providing good spatial resolution of the reflected light, these alternate techniques also have various limitations. The "Ward technique" 200, for example, requires mechanical motion of the light source 206, and requires that the sample 206 fit within the device. The "Marschner technique" 300 requires mechanical motion of the camera 304, and requires that the sample 302 be homogeneous and specially prepared. Both of these alternate techniques require a relatively large equipment setup, suitable for laboratory testing, but not suitable for portable or field use.

DETAILED DESCRIPTION

Photodiode-based BRDF measurement is described herein. In this description, examples are provided that utilize Light Emitting Diodes (LEDs), which are specific types of photodiodes. It is recognized that photodiodes in general may be utilized to implement the techniques described herein, and the description of embodiments that specifically utilize LEDs is not intended as a limitation.

By utilizing photodiodes, as described herein, smaller, even portable, BRDF measurement systems can be implemented. Such systems can conceivably be used to measure BRDF values for any type of surface, including human body parts, for example skin, for medical applications.

Figure 1:
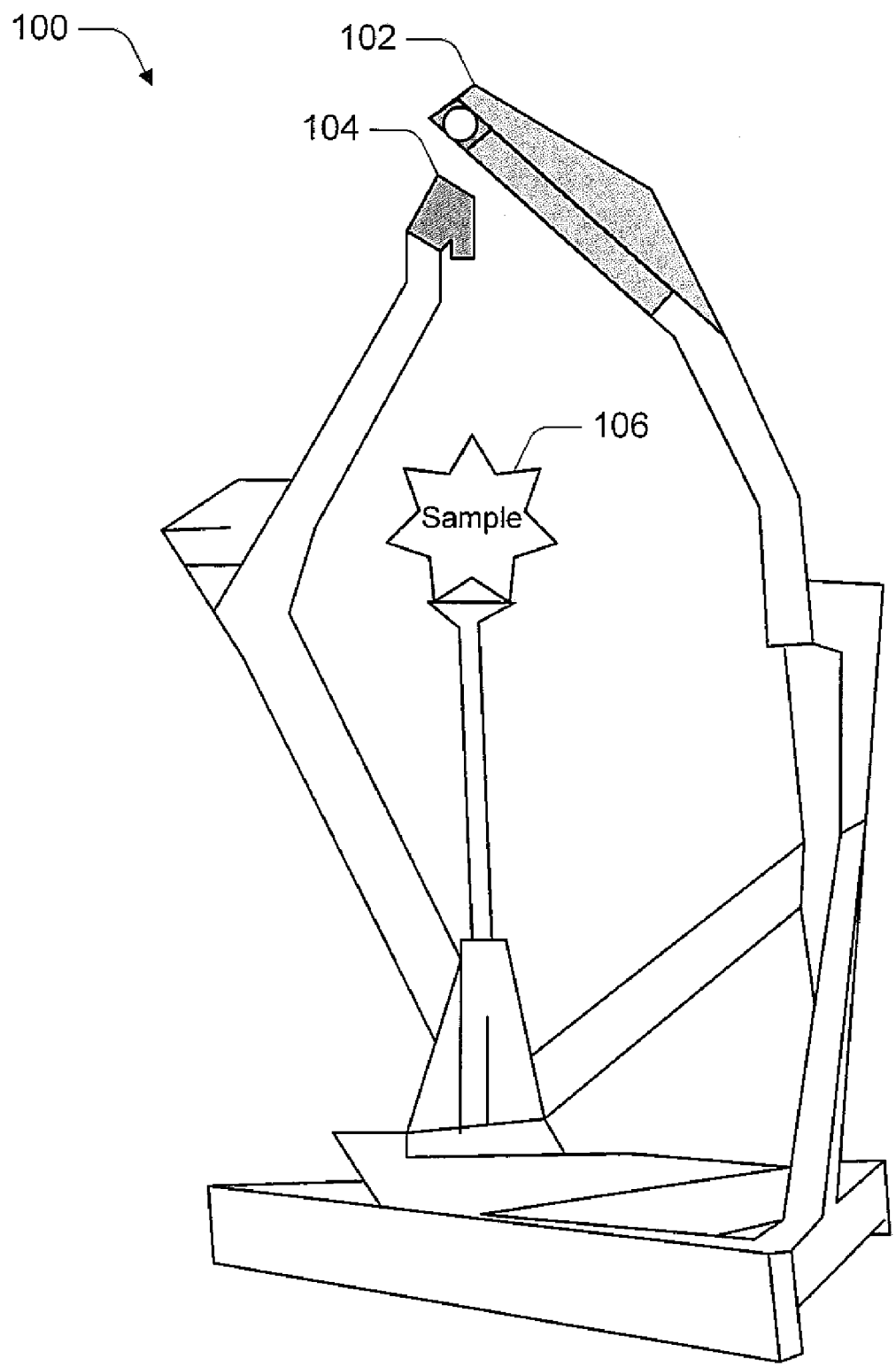
FIG. 1 (Prior Art) is a diagram of a conventional gonioreflectometer.
Figure 2:
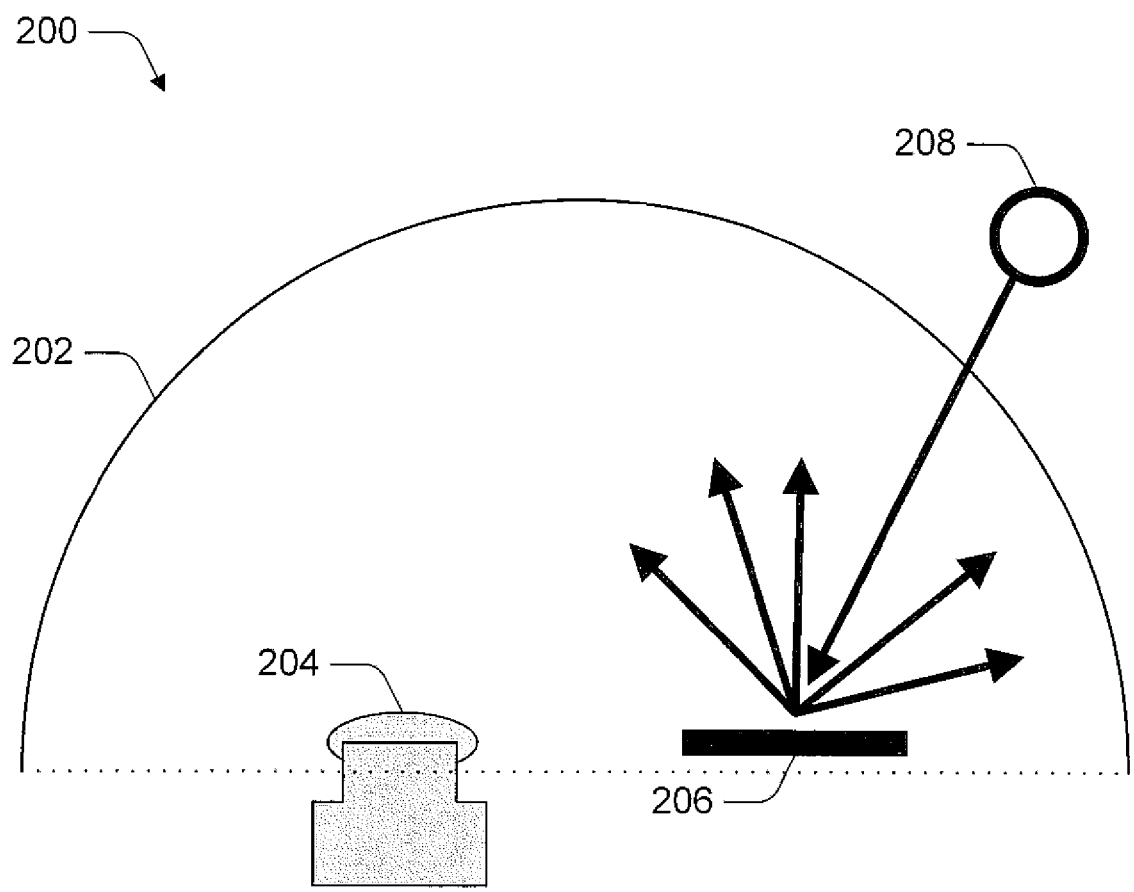
FIG. 2 (Prior Art) is a diagram of an alternate method of BRDF measurement.
Figure 3:
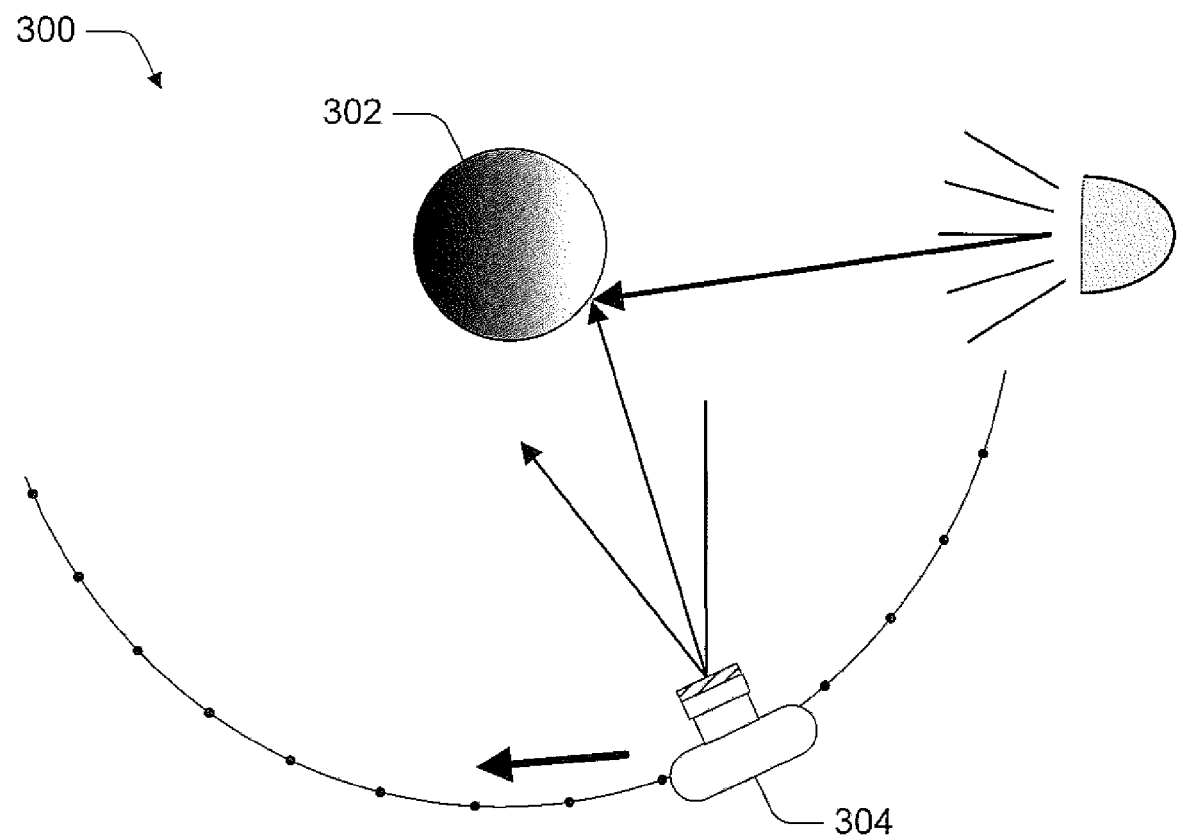
FIG. 3 (Prior Art) is a diagram of another alternate method of BRDF measurement.
Figure 4:
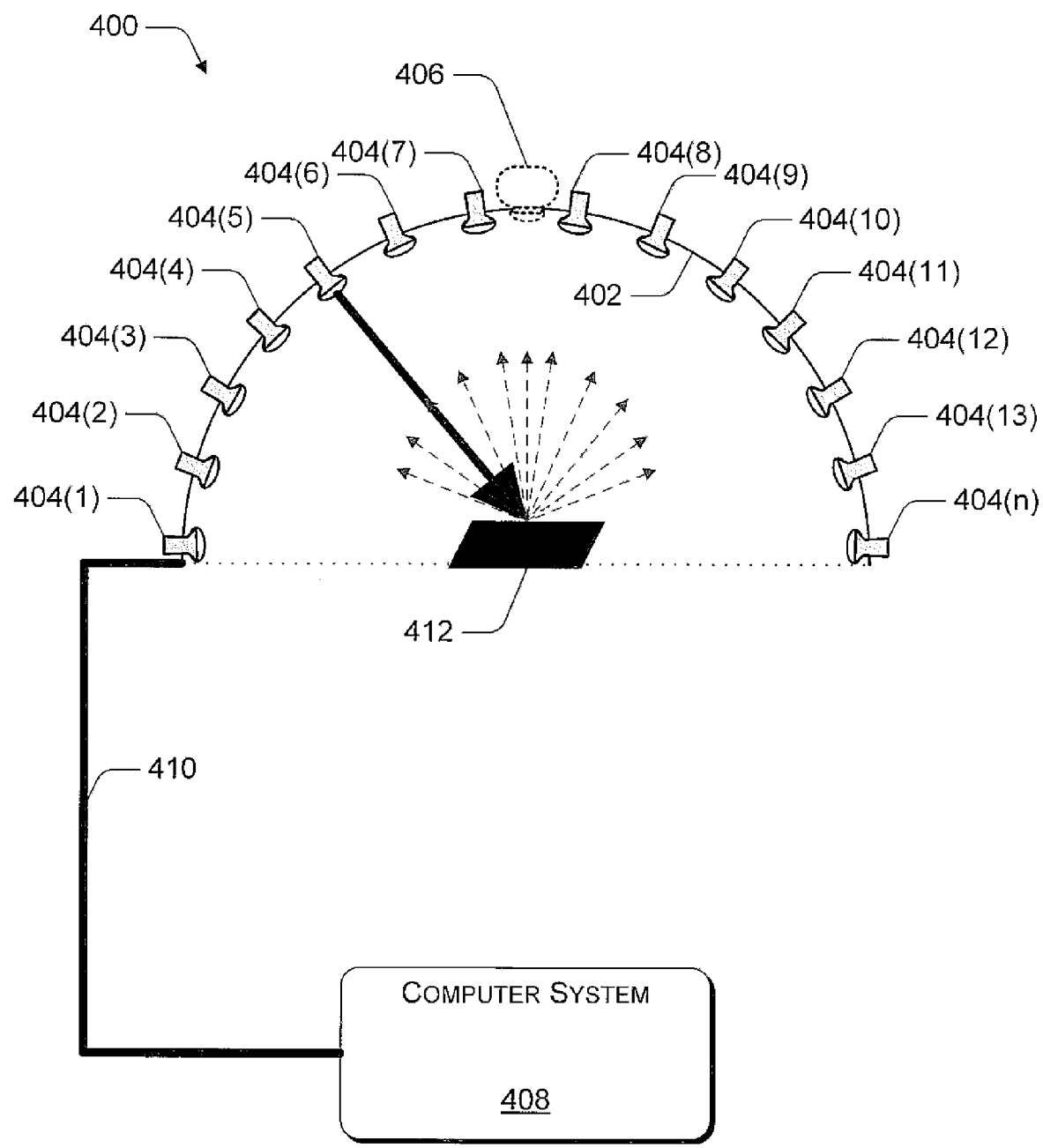
FIG. 4 is a diagram of an exemplary photodiode-based BRDF measurement device.

FIG. 4 illustrates an exemplary photodiode-based BRDF measurement system 400. Exemplary photodiode-based BRDF measurement system 400 includes measurement head 402, which houses multiple LED units 404; camera 406 (optional); and computer system 408, which is communicatively coupled to measurement head 402 via control/data lines 410.

Each of the LED units 404 can act as a light source and as a light detector, but in an exemplary implementation, not both at the same time. When one LED unit emits light, the other LED units act as light detectors and measure reflection. By assigning a different LED unit as the LED unit that emits light, it is possible to measure many combinations of light emission and reflection without any moving parts. This process is described in further detail below, with reference to FIG. 5.

In an exemplary implementation, optional camera 406 can be used to capture texture maps, which represent changes in texture based on changes of illumination direction. Camera 406 can also be used in photometric stereo to recover normal vectors to the surface given at least three different linearly independent illumination directions. Increasing the number of illumination directions increases the robustness of such an exemplary system.

Computer system 408 sends commands to the measurement head 402 and activates the LED units 404 one by one (or in groups to provide multiplexed illumination, as described in further detail below), either directly or via a control circuit located at the measurement head itself. The readings from the other (non-emitting) LED units are reported to the computer system 408, which then processes the signals according to calibration data to generate BRDF values. Computer system 408 may also be used to control optional camera 406 and to process multiplexed illumination data and super-resolution data, as described below.

Figure 5:
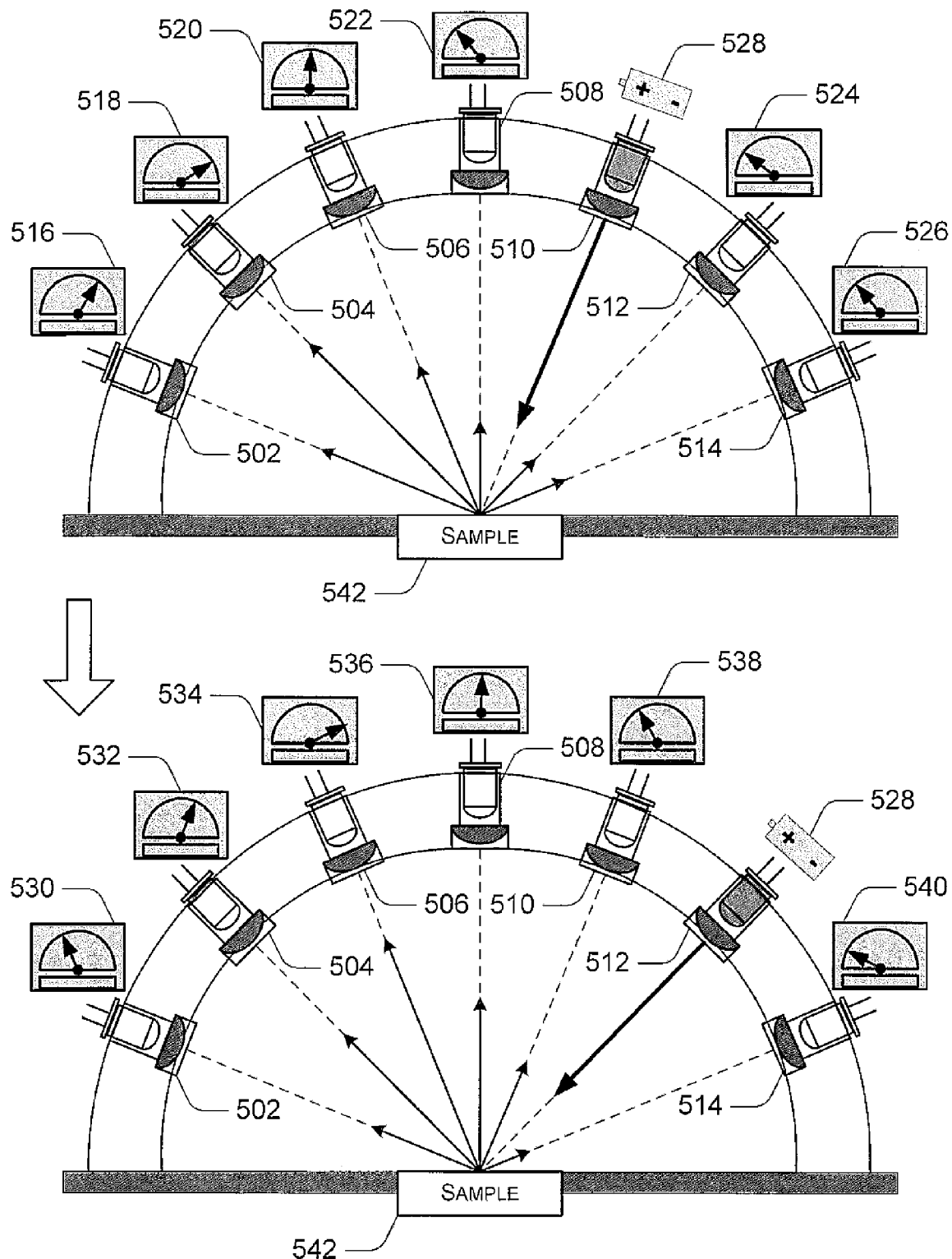
FIG. 5 illustrates measurement of reflected light using an exemplary photodiode-based BRDF measurement device.

FIG. 5 illustrates an exemplary process for utilizing an exemplary photodiode-based BRDF measurement device to capture BRDF values. As described above, when one LED unit emits light, the other LED units act as light detectors and measure reflection. For example, as shown in FIG. 5, LED unit 510 receives power, causing it to emit light, while LED units 502, 504, 506, 508, 512, and 514 each measure the reflected light. In FIG. 5, measurements 516, 518, 520, 522, 524, and 526 represent the reflection intensity measured by each of the detecting LED units. As shown in the lower portion of FIG. 5, after measurements 516-524 are taken, the power supply 528 is applied to LED unit 512, causing LED unit 512 to emit light. While LED unit 512 emits light, LED units 502, 504, 506, 508, 510, and 514 each measure the reflected light. In FIG. 5, measurements 530, 532, 534, 536, 538, and 540 represent the reflection intensity measured by each of the detecting LED units. This continues, with a different LED unit illuminating the sample 542 from a different angle, and the remaining LED units, including the previous illuminator, measuring the reflected light. This process is repeated until all desired light patterns have been activated.

Figure 6:
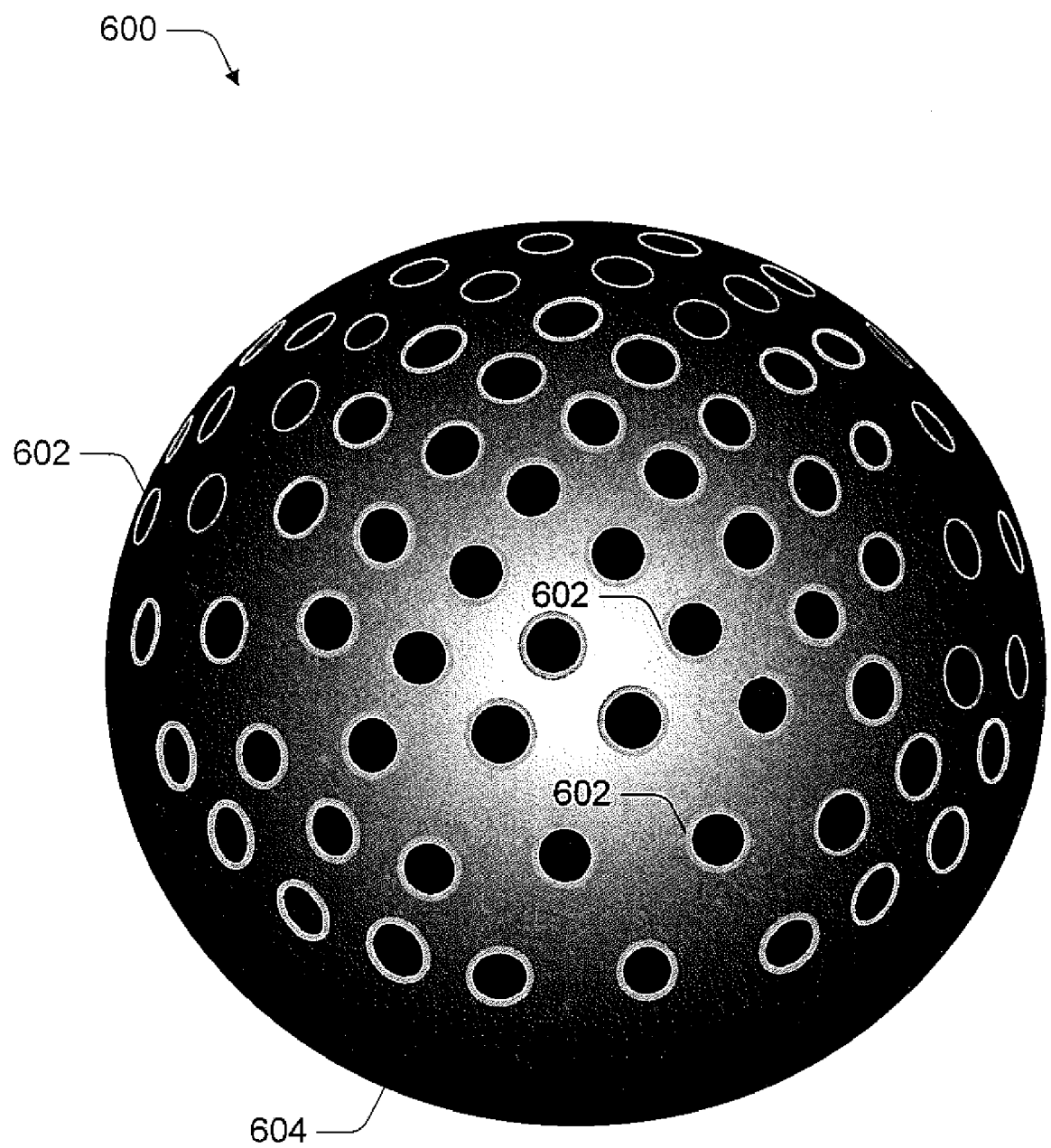
FIG. 6 is a diagram of a mount component of an exemplary photodiode-based BRDF measurement device.

FIG. 6 illustrates an exemplary hemispherical mount component 600 of measurement head 402. Mount 600 is similar to a compound eye in that it has many eyelets 602 arranged on a hemisphere 604. Unlike a compound eye, the eyelets 602 face the center of the hemisphere and are optically isolated from each other. In an exemplary implementation, each eyelet 602 houses an LED unit 404 with its own lens and a single sensing element, and can emit light as a focused beam directed at the center of the hemisphere. The hemispherical shape of the mount component 600 provides accurate geometrical alignment of the LED units 404, optical isolation between the LED units 404, and mechanical support for the LED units 404. In an exemplary implementation, mount component 600 is formed from a material that can transfer and radiate heat (e.g., a metal), which also provides heat sinking for the LED units 404.

Figure 7:
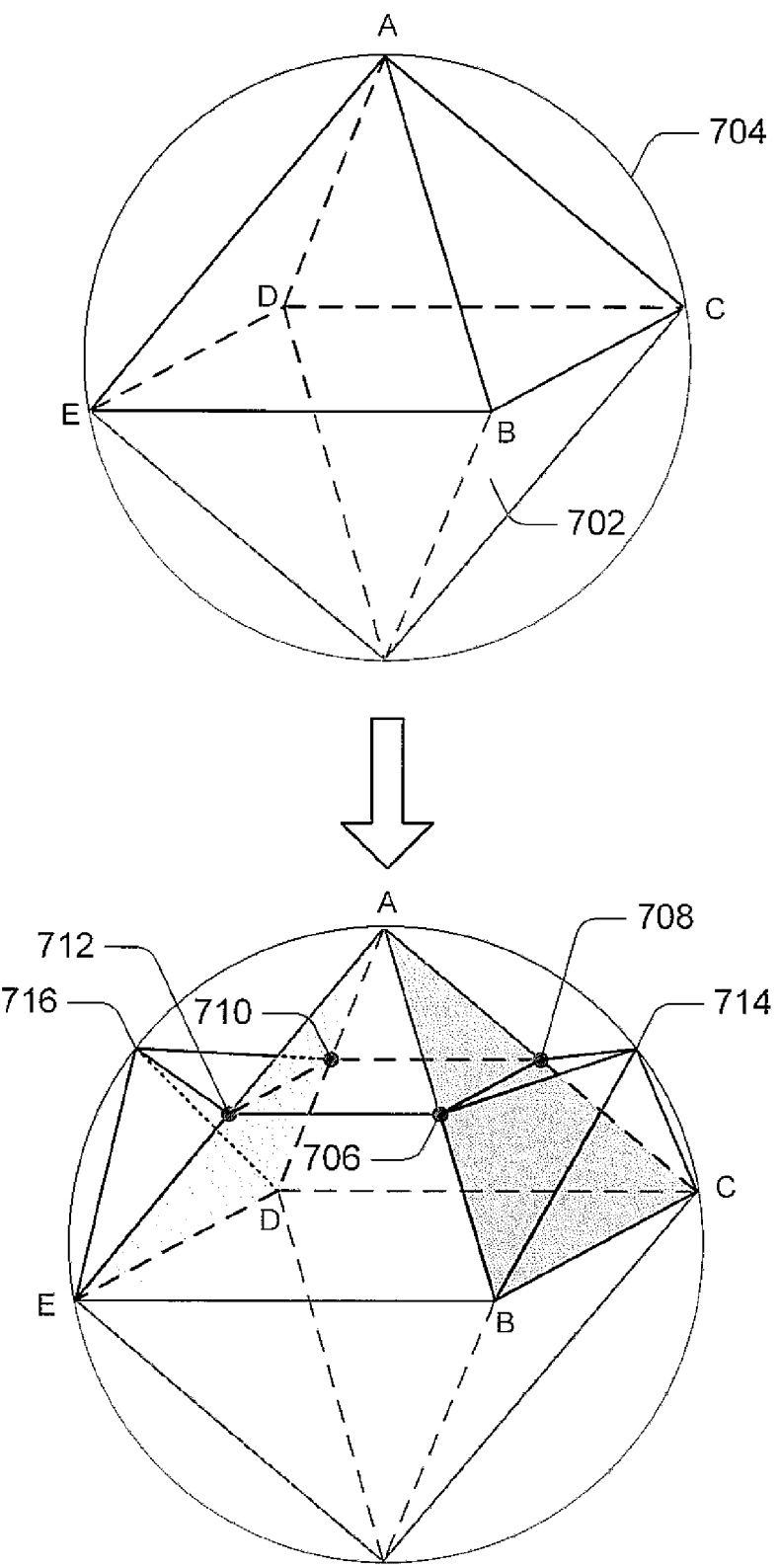
FIG. 7 is a diagram of an exemplary octahedron inscribed in a sphere, which may be expanded to determine placement of photodiode units.

In an exemplary implementation, eyelets 602, and thus the LED units 404, are distributed uniformly and symmetrically over the hemisphere. Geodesic tessellation may be used to produce uniform and symmetric distribution. FIG. 7 illustrates an exemplary use of geodesic tessellation using an octahedron 702 inscribed in a unit sphere 704 centered at the origin. Considering just the four upper triangular faces of the octahedron (and disregarding the bottom four), the midpoints of the edges (AB, AC, AD, and AE) are used to subdivide each of the four upper triangles. New triangles are then formed based on points B, C, D, and E, and midpoints 706, 708, 710, and 712. The new triangles formed by points B, C, 706, and 708 intersect the sphere at point 714. Similarly, the new triangles formed by points D, E, 710, and 712 intersect the sphere at point 716. Although not shown in FIG. 7, new triangles are similarly formed based on points C, D, 708, and 710, and also based on points B, E, 706, and 712. This process can be repeated, iteratively, for each existing triangle, thereby adding additional points of intersection with the sphere, which each indicate a location for an LED unit. In this way, the hemisphere is iteratively subdivided into finer and finer tessellations. This procedure produces $4^n$, n=1, 2, 3, . . . triangles on the hemisphere. The radius r of a sphere for housing LED units having diameter of d (enclosed within each triangle) is $r=((\sqrt{3})d)/2 \sin(\pi/(2n+1))$. The lengths of the edges can vary by a factor as high as 1.73, but finer tessellations reduce the impact of this non-uniformity. Using hexagonal lenses (or LED units), a better tessellation with a nearly 100% fill factor is possible using a hexagonal geodesic dome, much like arrangements of many compound eyes found in nature.

In an exemplary implementation, the mount component (the hemisphere) is machined from a single piece of aluminum using a computer numerical control (CNC) machine. This provides accuracy, mechanical strength, and heat dispersion for the LEDs. The hemisphere is painted matte black to reduce unwanted inter-reflections. The hemisphere is fitted with 86 eyelets, enabling a total of 7310 (86*(86−1)) possible illumination-reflection pairs. The exemplary mount component includes a controller that contains a signal amplifier, an A/D converter, a micro-controller, and a communication unit in one board. A second extension board contains LED control logic (multiple extension boards can be added to increase the number of LEDs). The controller receives a sequence of illumination patterns from a host computer via an RS232 connection, executes them one by one, and sends the measurements back to the host for processing. The speed of the measurement device is limited by the communication speed to the host.

Figure 8:
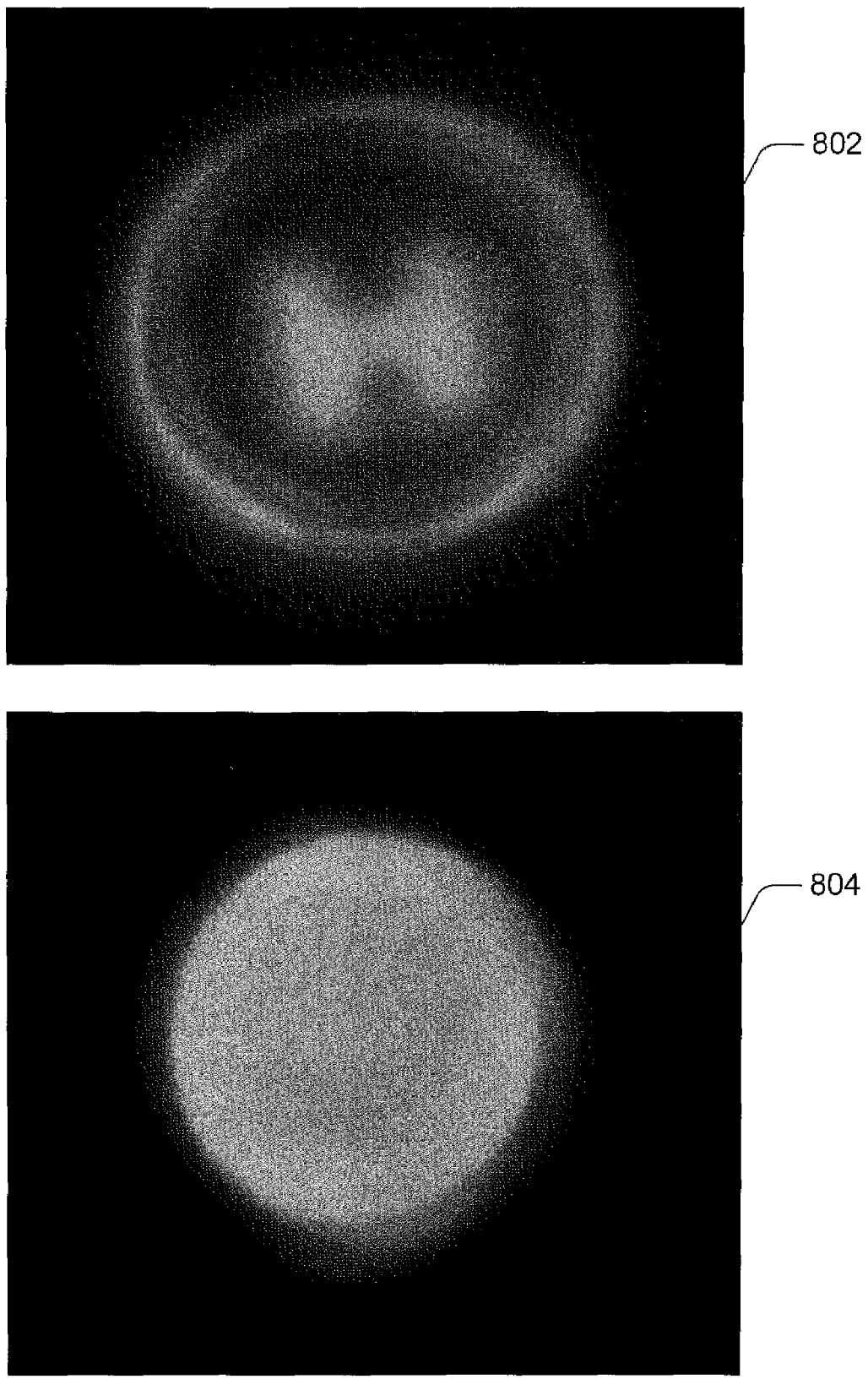
FIG. 8 is a pair of images of light emitted from a particular LED, one without a lens, and one with a lens.

For effective BRDF measurement, uniform illumination of the sample surface is desired. Different LEDs, however, produce very different illumination patterns, even for the same rated view angle. Furthermore, an LED usually creates an image of the emitting element, which is also undesirable for BRDF measurement (i.e., a flat uniform light is preferable). FIG. 8 illustrates improvement in the uniformity of illumination that can be achieved by using a lens in conjunction with an LED. Image 802 is an image of light emitted from an exemplary LED without a lens. In contrast, image 804 is an image of light emitted from the same LED with a lens.

Figure 9:
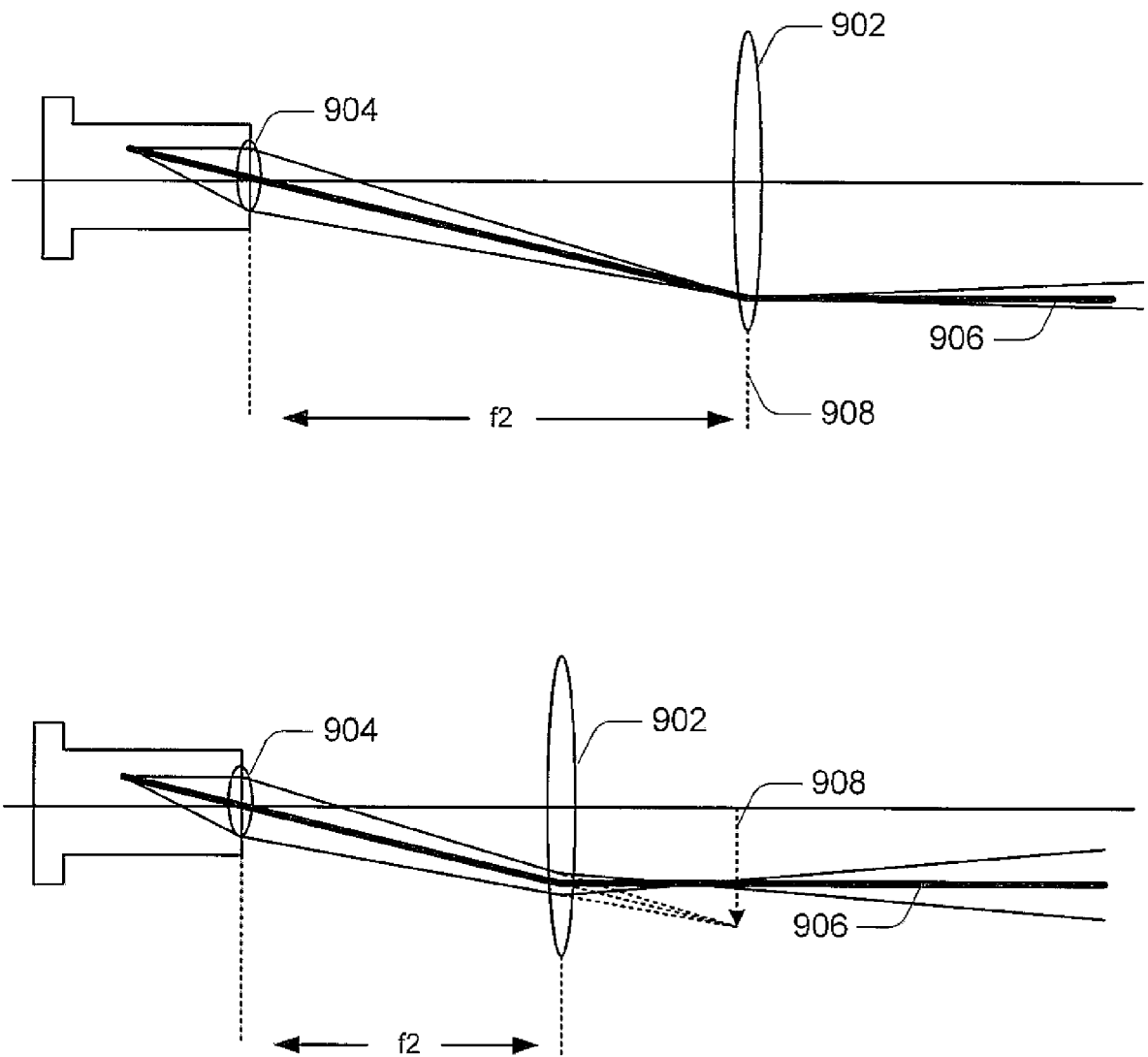
FIG. 9 is a diagram of exemplary light beam shaping.

FIG. 9 illustrates how adding a lens to an LED can be used to reshape the light beam emitted from the LED. Adding a convex lens 902 in front of the LED 904 at distance f2 from the LED's aperture, where f2 is the focal length of the added lens, creates a telecentric projection of the chief ray 906. The top portion of FIG. 9 shows the lens 902 located at the image plane 908 of the lens. By changing f2, the diameter of the beam can be controlled. A certain amount of defocusing can be desirably achieved to contribute to diffused illumination. The bottom portion of FIG. 9 shows the lens 902 located closer than the image plane 908. In both setups, only the chief ray 906 is telecentric—the beam can still be out of focus, but will keep its size. This allows the creation of a uniform circle of illumination, as shown in image 804 of FIG. 8.

Figure 10:
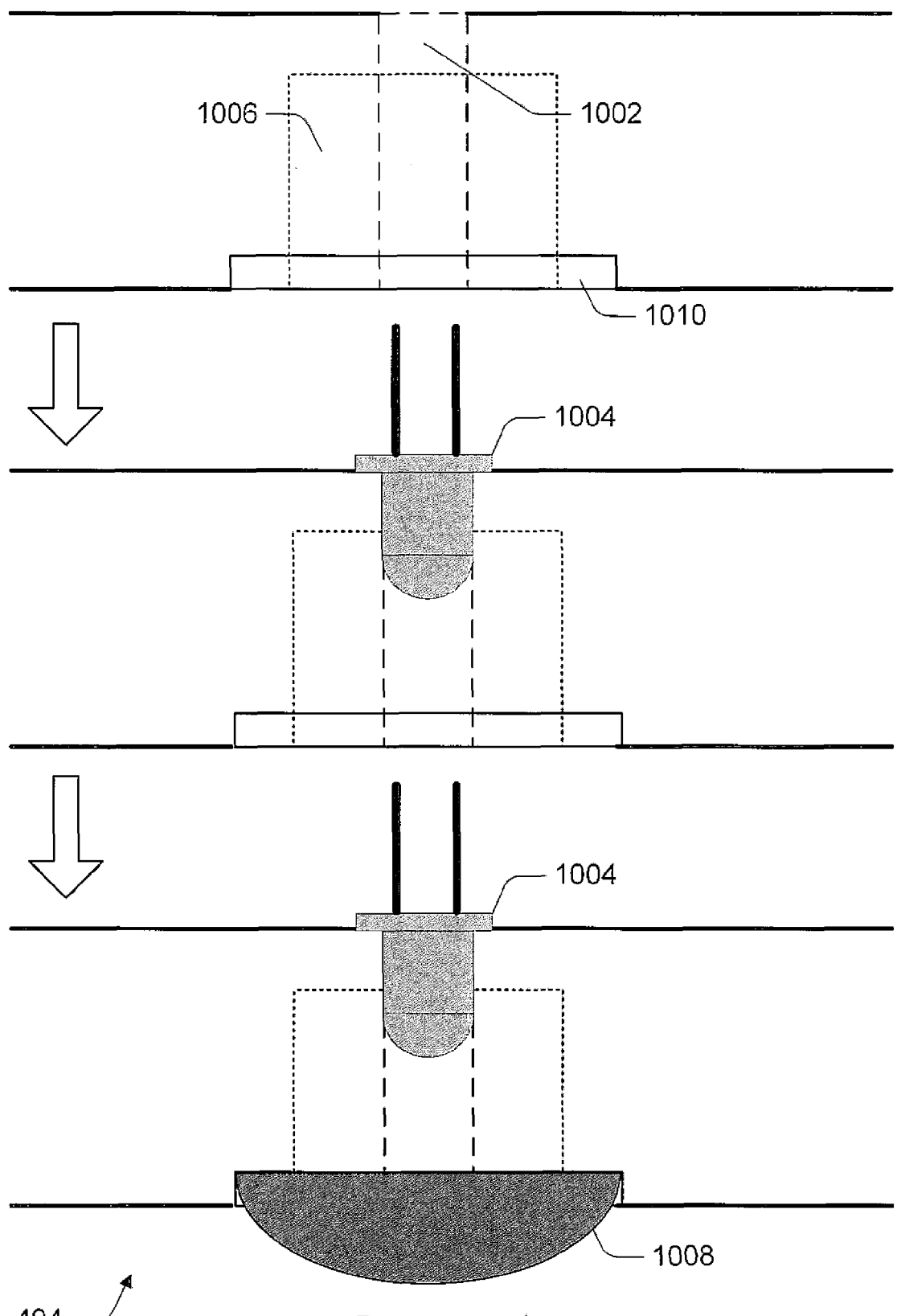
FIG. 10 is a diagram of an exemplary structure of an LED unit.

FIG. 10 illustrates an exemplary structure of an LED unit 404. Exemplary LED unit 404 consists of three concentric holes of varying depths and diameters. For example, the deepest and narrowest hole 1002 (depicted with a large dashed line) is, for example, 3 mm or 5 mm wide to accommodate a conventional LED 1004 and holds the LED 1004 firmly (and may also act to cool the LED). A second, or middle hole 1006 (depicted with a small dashed line) is shallower than topmost hole 1002, but has a larger diameter, allowing light from the LED 1004 to reach an added lens 1008 without interference. A third, or lowest hole 1010 (depicted with a solid line), which may have the largest diameter, is used to keep the lens 1008 firmly at the appropriate distance from the LED 1004.

In an exemplary implementation, the lenses for each of the LED units is constructed as a Fresnel type lens, in which case, the base (the hemisphere) and the lenses can be molded into two (e.g., plastic) parts—an opaque base and a transparent lenslet array attached to the base.

Figure 11:
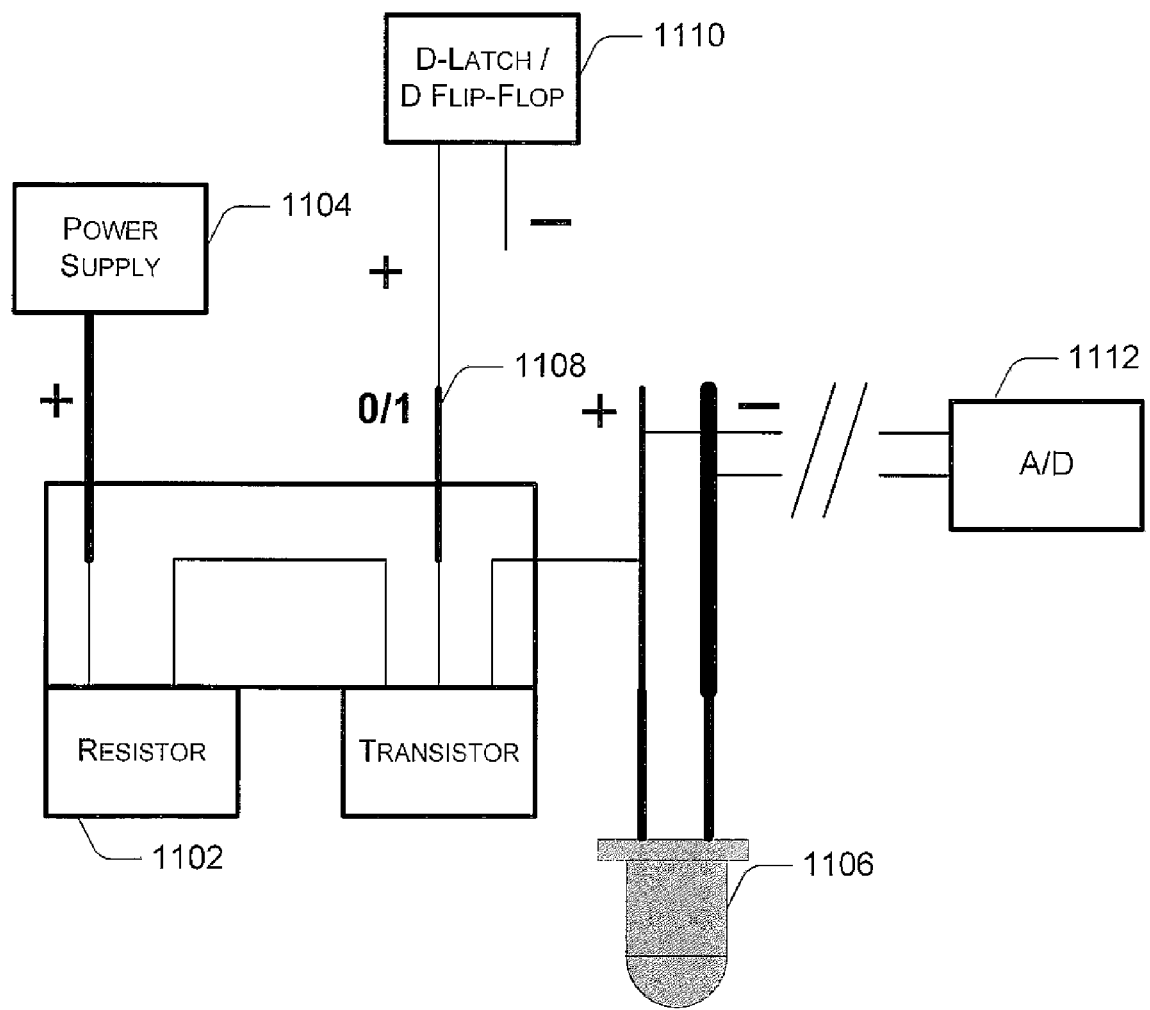
FIG. 11 is a diagram of an exemplary driving circuit for one LED.

FIG. 11 is a diagram of exemplary connections to an exemplary LED. Power is received at resistor 1102 from a common external power supply 1104. The LED 1106 is controlled by a logic line 1108. D-Latch (or D flip-flop) 1110 maintains the status of the LED. Analog-to-digital converter 1112 is used to measure voltage of the LED. Although not shown, routing circuitry and/or a signal amplifier may be placed between analog-to-digital converter 1112 and LED 1106. In an exemplary implementation, although not shown in FIG. 11, communication with computer system 408 is supported by address lines, data lines, and select read/write lines (e.g., write turns the LED on/off, and read returns the LED voltage).

Using an LED as both a light source and as a light detector poses challenges. An LED is a photodiode specially optimized for the purpose of emitting light, but also preserves its functionality as a photodiode. Therefore, an LED can also be used as a light detector. LEDs have been used in low-cost communication devices, as light sources and as light detectors. However, when functioning as a light detector, an LED typically provides only binary (0, 1) detection (i.e., the LED detects that there is light or there is not light). But like other photodiodes, LEDs can be used as an analog device to measure different levels of incident light.

Figure 12:
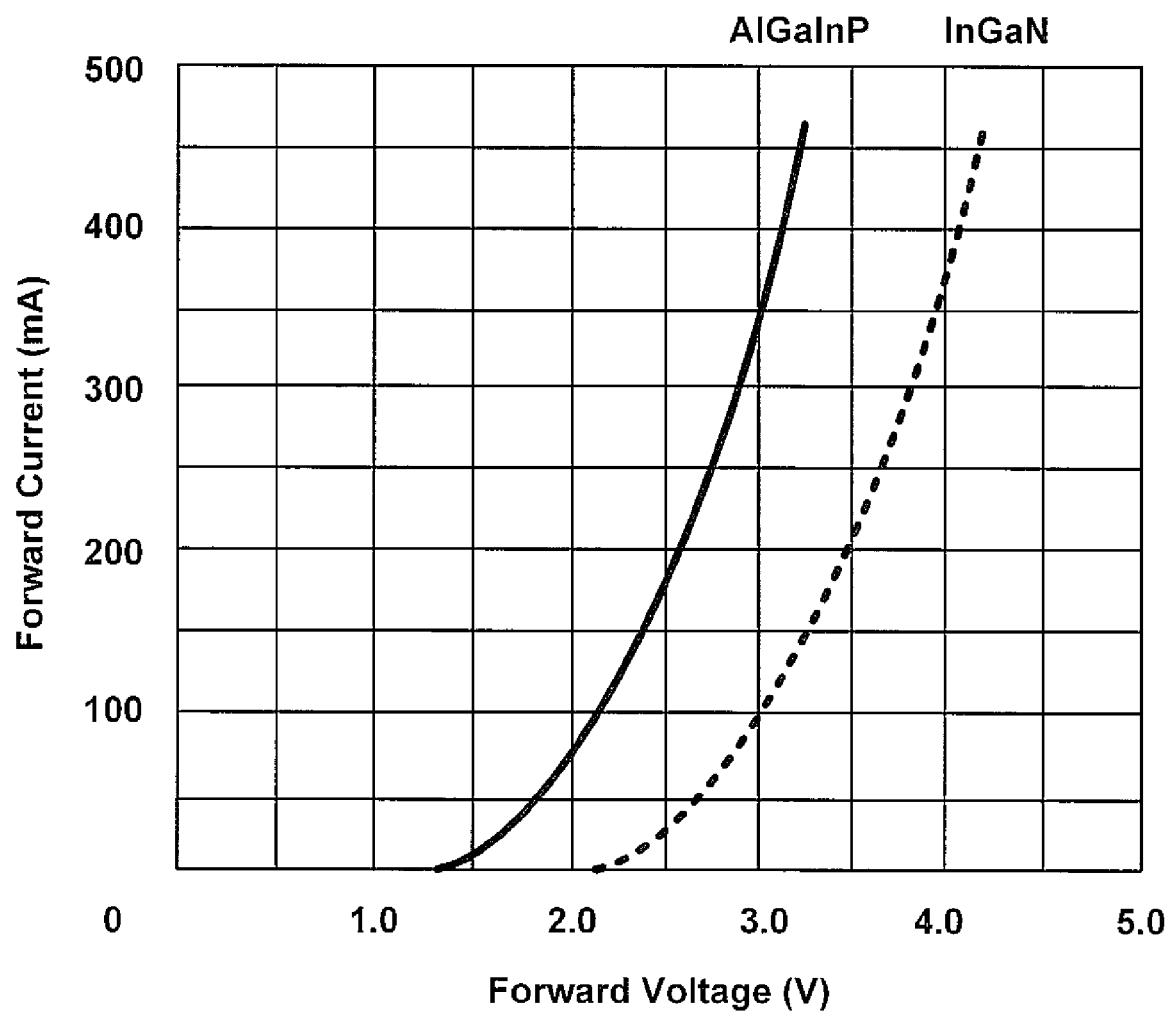
FIG. 12 (Prior Art) is a diagram of conventional relationships between LED voltage and current.
Figure 13:
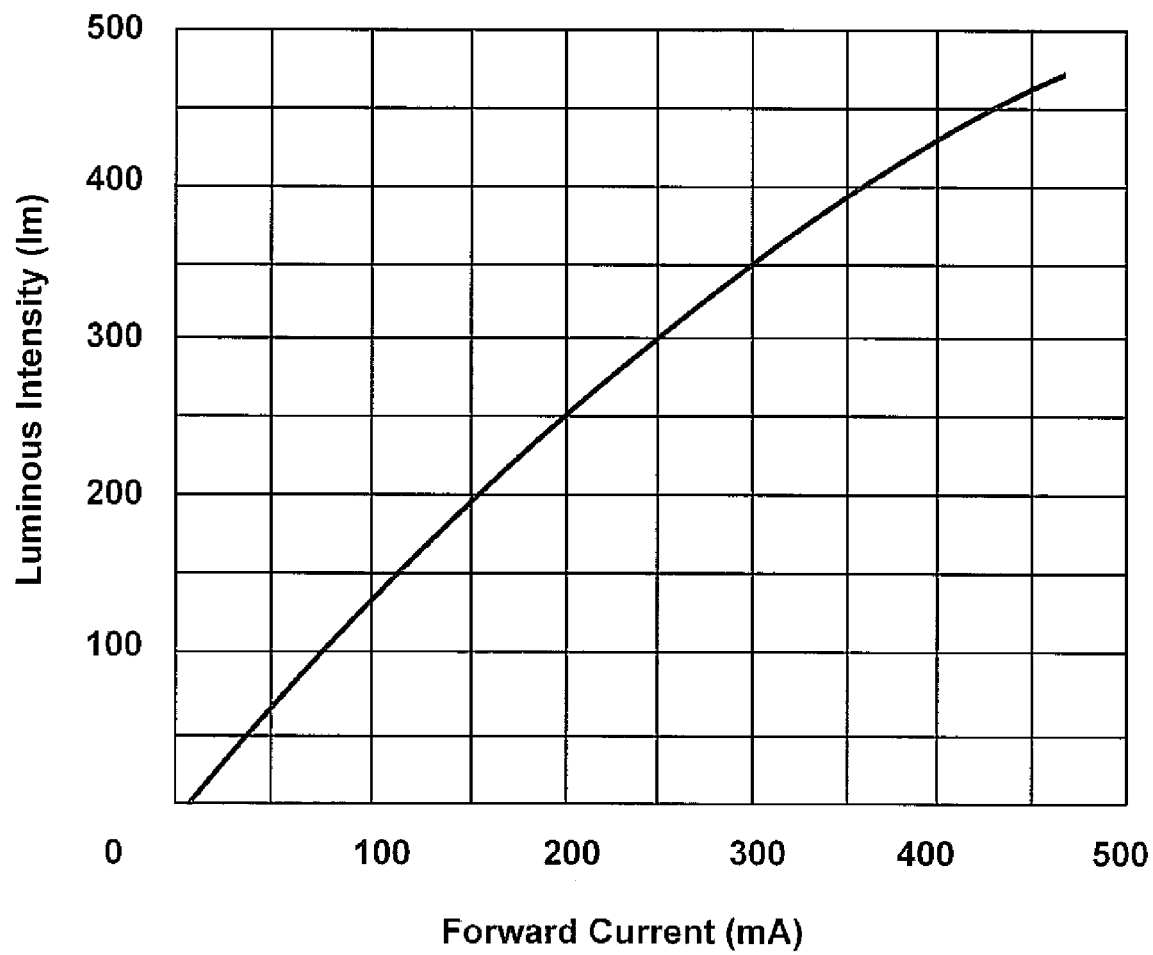
FIG. 13 (Prior Art) is a diagram of conventional relationships between LED forward current and luminous intensity.

LEDs can include different semiconductors, including, for example, Silicon (Si), Gallium Arsenide (GaAs), Gallium Nitride (GaN), Gallium Phosphide (GaP), Gallium Arsenic Phosphide (GaAsP), Aluminum Gallium Indium Phosphide (AlGaInP), Indium Gallium Nitride (InGaN), and Aluminum Gallium Arsenide (AlGaAs), each having different electro-optical properties with regard to wavelength, sensitivity, operational voltage, and dynamic range. FIG. 12 illustrates relationships between current and voltage for exemplary LEDs. Specifically, the relationship between voltage and current is illustrated for an InGaN blue LED and for an AlGaInP red LED. FIG. 13 illustrates the relationship between forward current and luminous intensity for an exemplary LED. As shown in FIGS. 12 and 13, the current is not linear with respect to voltage, but, assuming constant temperature, the relationship between the emitted light and the current is nearly linear over a small range of current values. Relationships between current and voltage and between current and intensity are usually given by the LED manufacturer.

Because LEDs are not optimized to be used as photodetectors, manufacturers do not provide specifications regarding an LED's response function, spectral sensitivity, or dynamic range. While this information is not provided by the manufacturer, it can be determined by calibration. In general. LEDs are sensitive to light of the same wavelength they emit, or shorter wavelengths. Hence, a red LED will responds to light emitted from a green LED or from a blue LED, but not vice versa.

High-dynamic range photosensors enable capture of a wide range of BRDF measurements. Several definitions of "dynamic range" are used throughout the industry. As used herein, to compare sensors with different characteristics, dynamic range is defined as $\log_2(I_{max}/I_{min})$, where $I_{max}$ is the maximum intensity level (just before saturation) that a sensor can measure, and $I_{min}$ is the minimum level (just noticeable) above 0 that a sensor can measure. This definition is also known as the range of f stops or the range of shutter stops, and is intuitive for image sensors and applies to other sensors equally well.

In an exemplary implementation, to measure an LED's dynamic range, the LED is placed in front of a strong light source (e.g., a halogen light with a condenser lens). The light is attenuated using different neutral density filters, and the voltage output of the LED is measured. Exemplary results are summarized in Table 1.

TABLE 1

| LED | λ | $V_{min}$ | $V_{max}$ | Att | DR |
| --- | --- | --- | --- | --- | --- |
| Blue | 465 | 3 | 2300 | 1/4096 | 12 |
| Green | 525 | 5 | 1930 | 1/8192 | 13 |
| Yellow | 590 | 320 | 1740 | 1/8192 | 19* |
| Red | 625 | 430 | 1650 | 1/8192 | 20* |

(*values are estimates)

In Table 1, λ represents the peak emitting wavelength of the LED. and $V_{max}$ is the maximum readout in millivolts. $V_{min}$ is the minimum measurable readout (i.e. higher than the readout in darkness) after applying the greatest attenuation. Att is the maximal attenuation used, and DR is the dynamic range expressed in f-stops. The measured dynamic range of these LEDs ranges from 12 to 20 f-stops, which is very high, for example, compared to the dynamic range of consumer cameras, which typically range between 6 and 8 f-stops. In this example, the dynamic range for the yellow and red LEDs has been estimated based on the linear response of the LED in this range, due to an inability of a filter to sufficiently reduce the signal level. It is recognized that several other methods may also be used to determine an LED's dynamic range, and the description above is for just one example method.

An LED's response function enables conversion of the LED's measured voltage to a linear irradiance value. To determine a response function for each particular LED, a white LED is placed inside an integrating sphere as a source, and the particular LED being measured (blue, green, yellow, or red) is placed inside the integrating sphere as the detector. Using a regulated power supply, different current levels are driven through the white LED. Keeping the current relatively low ensures that the white LED operates in the approximately linear region shown in FIG. 13. Because the source LED radiance varies approximately linearly with current, measuring the detector voltage for each source current gives the detector's response function, at least in response to white light. Depending on the equipment available, more accurate measurements may be obtainable.

Figure 14:
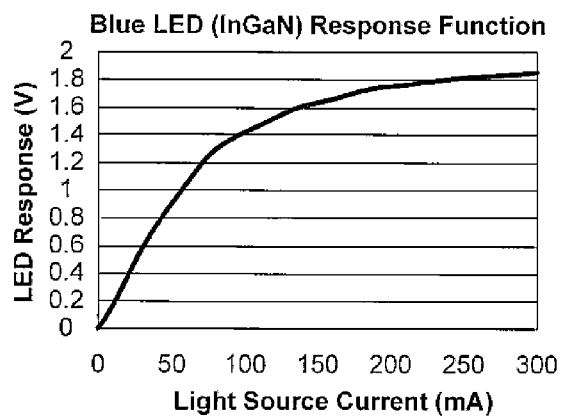
FIG. 14 is a collection of charts illustrating exemplary measured LED response curves.
Figure 14:
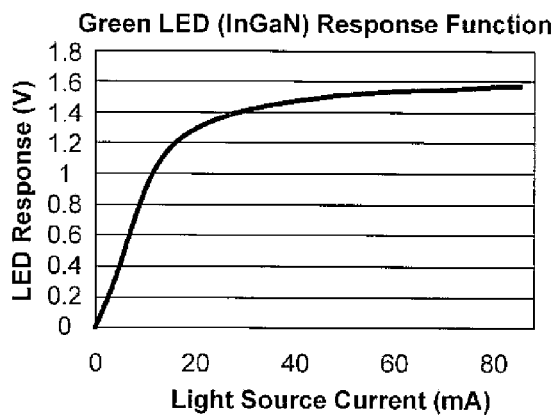
Figure 14:
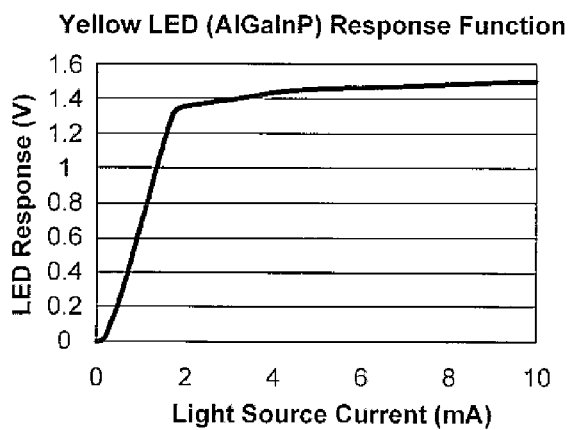
Figure 14:
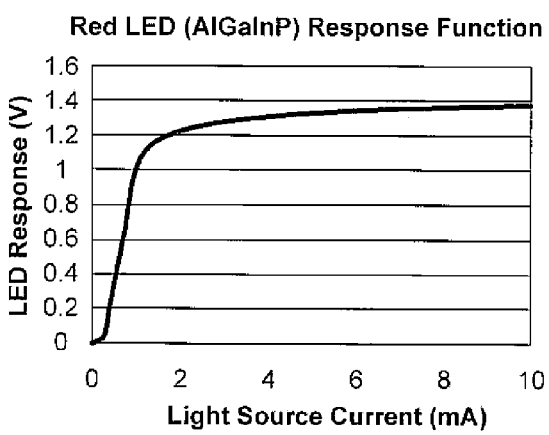

Exemplary measured response curves are shown in FIG. 14. Each of the measured LEDs has a highly non-linear response, which explains their high dynamic range, but also suggests that the accuracy of their measurements decreases at higher irradiances. A shown in FIG. 14, the blue and green LEDs (InGaP) are less sensitive, and their responses rise less sharply, than the red and yellow LEDs (AlGaInP).

While each LED's response function provides a means for recording a measurement from the LED, several other measurements are initially determined to calibrate the BRDF system to enable more accurate BRDF measurements. These measurements may include any combination of relative responses between each pair of LEDs, a measurement of dark current associated with each of the LEDs, variance between responses by LEDs of the same type, and stray light measurements for each emitter/detector combination.

Measuring relative responses between each pair of LEDs provides for adjustments in recorded measurements based on which LED was acting as an emitter and which LED the measurement was recorded from. As discussed above, in general, LEDs are sensitive to wavelengths equal to or shorter than the wavelength of the light they emit. Since LED spectra are not delta functions, LEDs with similar peak emission frequencies (such as the described red and yellow LEDs) can sense each other, but their responses are different. Using a similar methodology to that described above or determining response functions based on white light, the response of each color LED to other colors capable of exciting it are measured.

LEDs, like the photodetectors in CMOS (complementary metal-oxide-semiconductor) and CCD (charge-coupled device) image sensors, generate a small amount of current even in darkness. This current results from thermal energy, not incident light. The dark current is modeled by a temperature dependent Poisson distribution. To measure the mean (which is also the variance) of this dark current bias, many measurements in complete darkness are averaged. The average is acceptable because the response functions of the LEDs are nearly linear at low current levels. The noise values are converted to irradiance space using the inverse response function. These irradiance values are then subtracted from later applied irradiances, including any subsequent calibrations that include a dark current component.

Multiple LEDs of a given color should provide the same measurement of reflection intensity from the same surface. However, because of geometric inaccuracies and photoelectric variations, LEDs of the same color may record varying measurements. To measure such variance, in an exemplary implementation, the bottom half of a small spherical diffuser is covered with reflective material and placed at the center of the BRDF measurement system. The surface of a white LED is sanded to better diffuse the light it emits, and the white LED is placed at the bottom of the diffuser. A baffle is inserted to prevent the white LED from directly illuminating the top half of the diffuser. The spherical diffuser both integrates and diffuses the light, so the result is a nearly isotropic light source over the top hemisphere of the diffuser. Measurements from each of the LEDs are then recorded, and variations between LEDs of the same color are measured and recorded for later compensation.

Figure 15:
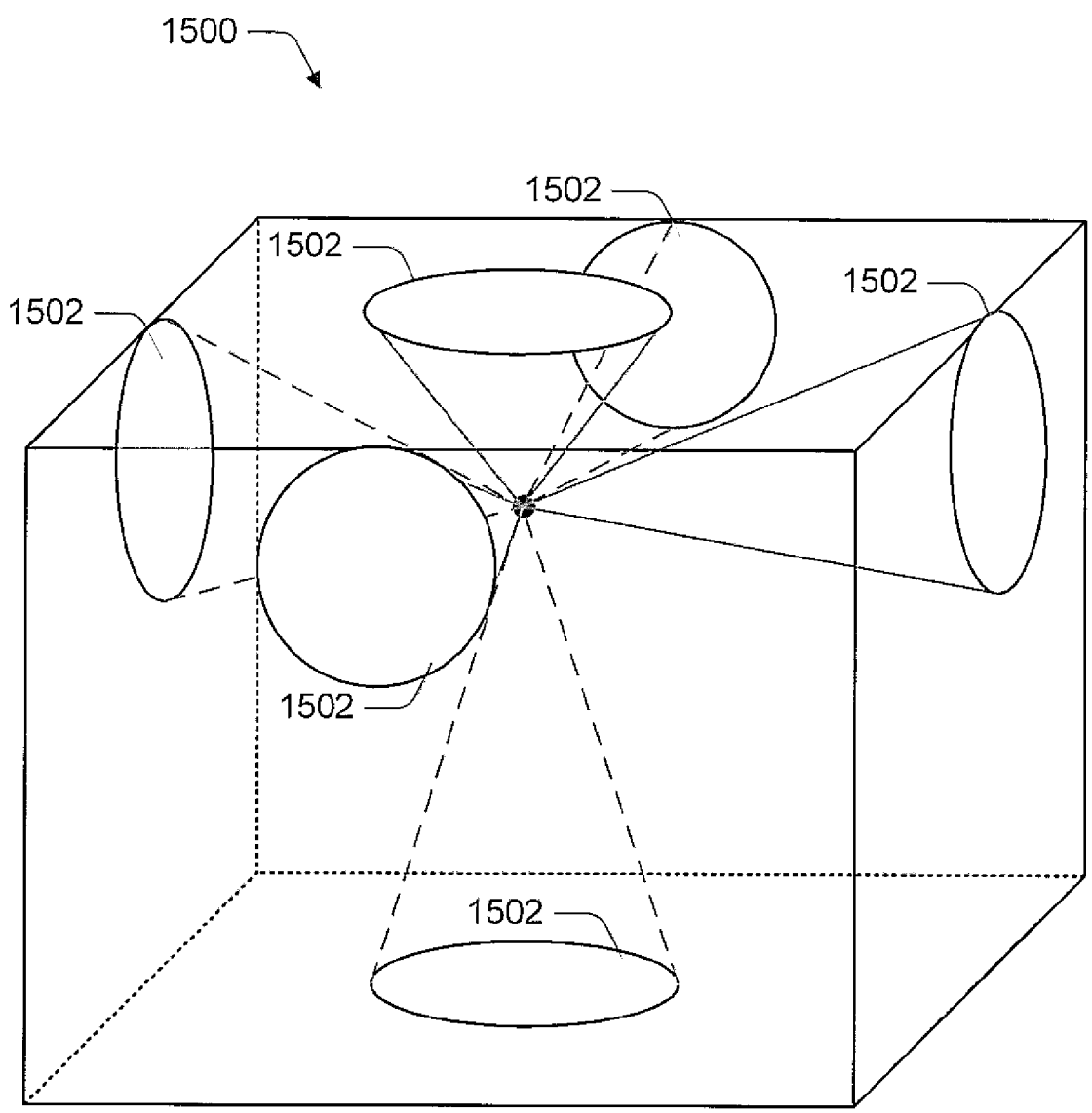
FIG. 15 (Prior Art) is a diagram of escape cones of an exemplary rectangular LED.

Stray light and internal scattering can also be an issue in capturing BRDF measurements as described herein. The physics of light emission from LEDs is such that light can escape the die only at certain specific angles called escape cones. FIG. 15 shows an example for a rectangular die 1500, which has one escape cone 1502 on each face.

Figure 16:
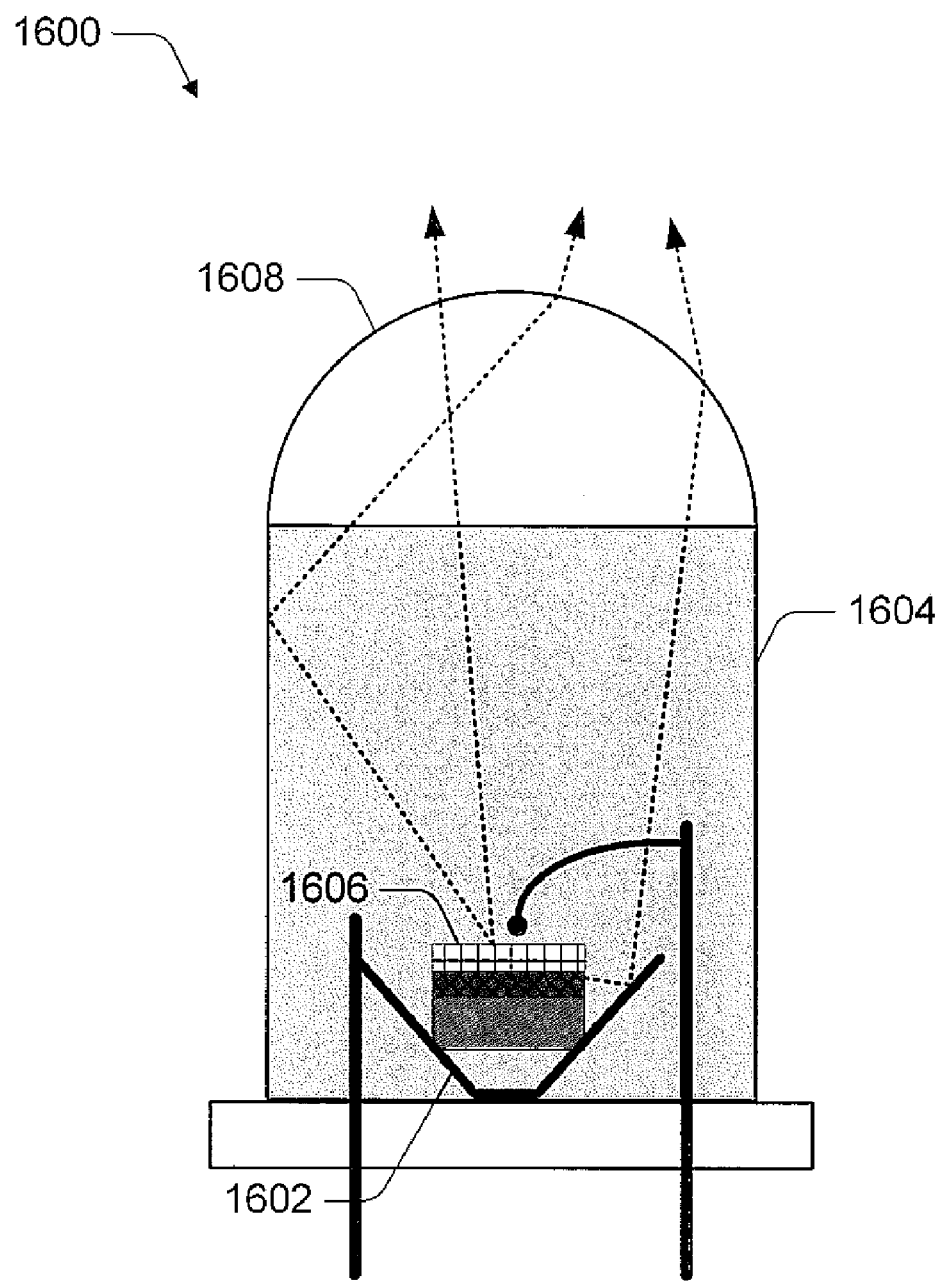
FIG. 16 (Prior Art) is a diagram of an exemplary T-1 LED.

An exemplary T-1 LED, shown in FIG. 16, includes a small reflector 1602 and an epoxy housing 1604, which work together to shape the light beam emitted by the photodiode 1606 toward a lens 1608.

Recognizing that some light escapes through the sides and back of an LED, minimizing and accounting for stray light from an emitting LED being detected by a sensing LED can increase the accuracy of recorded BRDF measurements. The structure of LED units 404, described above, helps to minimize interference caused by stray light emitted from an LED. For example, as described above with reference to FIG. 10, hole 1006 allows light from the LED 1004 to reach lens 1008 without interference. Furthermore, in an exemplary implementation, the inner surface of hole 1006 (and also the entire inner surface of the hemisphere) is coated with a black coating (e.g., color or anodized) to minimize reflection.

Figure 17:
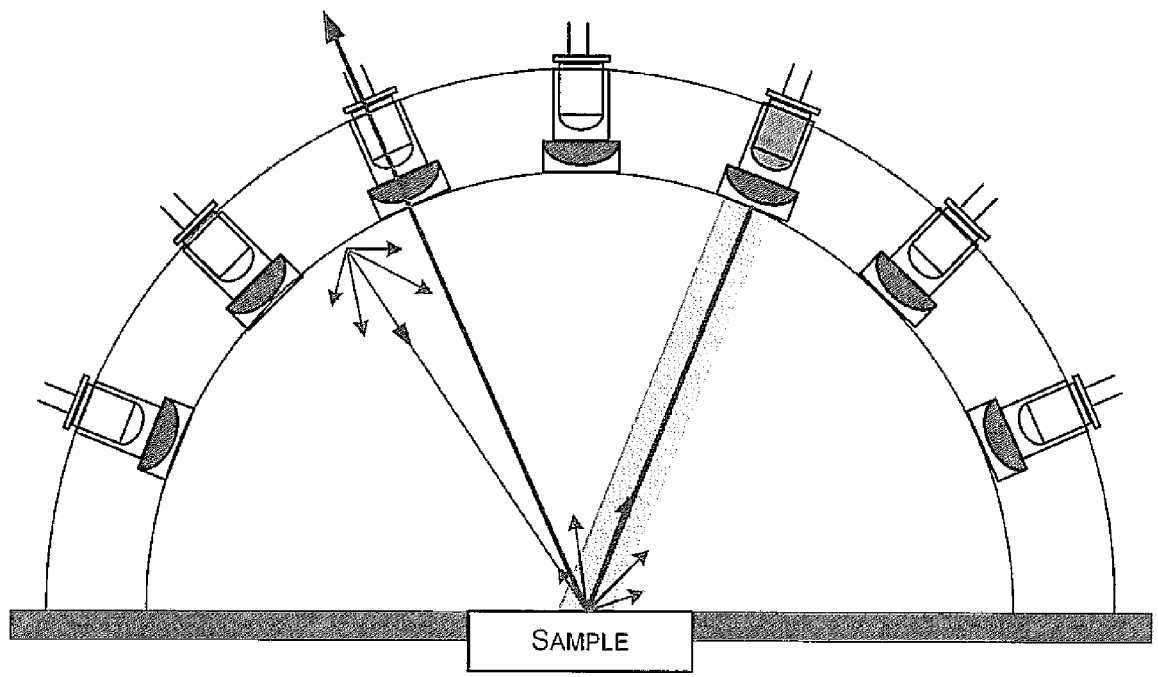
FIG. 17 is a diagram of exemplary undesirable reflections and light scattering within an exemplary photodiode-based BRDF measurement device.

However, the physical structure of LED units 404 may not eliminate all of the stray light. In an exemplary implementation, to account for any remaining stray light, a light trap is placed at the material sample location and signals are measured and recorded for each LED emitter-detector combination. This enables cancellation of stray light that exists in the measurement device. However, there can still be unwanted secondary and higher order reflections inside the hemisphere. FIG. 17 illustrates such undesirable reflections and light scattering. However, in the exemplary implementation described herein, eyelet placement and telecentric optics significantly reduce detectors' sensitivity to non-radial rays. For radial rays, most of the light that enters an eyelet is either absorbed or passes through (e.g., into a dark room or box). Depending on the fill factor, some of the light will hit the hemisphere black wall. Due to the geometry of the device, most of the non-absorbed part will be retro-reflected back to the illuminating LED, which is not measuring any reflectance. This limits the unwanted stray light to the diffused part of third or higher order reflections.

The calibration measurements that are recorded, as described above, are used by computer system 408 to adjust BRDF measurements received from detecting LEDs. For example, received BRDF measurements are adjusted based on previously recorded calibration measurements of relative responses between each emitter/detector pair of LEDs, dark current, response variations, and stray light for each emitter/detector pair of LEDs. Adjusting measurements received from detecting LEDs based on the previously recorded calibration recordings results in the desired BRDF values.

In an exemplary implementation, if the light emitted by a single LED proves to be too dim, it is possible to light multiple LEDs and then de-multiplex the illumination. Such multiplexing in support of BRDF measurement constitutes a new use for multiplexing.

Multiplexed illumination increases the measurement signal to noise ratio (SNR). Because each emitting LED cannot be used as a detector, multiplexing using the described measurement device is more complex. The basic equation system for recovering the BRDF is:

$$\begin{bmatrix} m_1 \\ m_2 \\ \vdots \\ m_n \end{bmatrix} = \begin{bmatrix} b_{11}*r_{11} & b_{12}*r_{12} & \cdots & b_{1n}*r_{1n} \\ b_{21}*r_{21} & b_{22}*r_{22} & \cdots & b_{2n}*r_{2n} \\ \vdots & \vdots & \vdots & \vdots \\ b_{n1}*r_{n1} & b_{n2}*r_{n2} & \cdots & b_{nn}*r_{nn} \end{bmatrix} \begin{bmatrix} \cos\theta_1 L_1 \\ \cos\theta_2 L_2 \\ \vdots \\ \cos\theta_n L_n \end{bmatrix}$$

where $m_i$ is the measured value at LED i, and $b_{ij} \in \{0,1\}$ indicates the LEDs activated for each basis vector. $r_{ij} = \alpha_{ij} f_{r(ij)}$ is the BRDF coefficient $f_{r(ij)}$ to be determined, multiplied by the known calibration factor $\alpha_{ij}$ of the i,j LED pair. $L_i$ is the intensity of LED i, and $\theta_i$ is the incident angle of LED i.

For n LEDs, there are $(n^2-n)/(n-b)$ unique BRDF coefficients to determine. $f_{r(ij)} = f_{r(ji)}$ due to BRDF reciprocity, and $f_{r(ii)}$ is not determinable because the retro-reflective ray cannot be measured by the LED emitting light. If b LEDs are on, only (n−b) measurements are obtained, and the number of different illumination patterns is $(\frac{1}{2}(n^2-n))/(n-b)$.

The optimal multiplexed illumination basis is based on a Hadamard code of length n+1, where (n+1)/4 is an integer. This basis consists of n different illumination patterns for n LEDs. For each measurement, (n+1)/2 LEDs are on and (n−1)/2 are off. If b=(n+1)/2, then the number of illumination patterns for the device described herein, using optimal illumination, is exactly n. These are the patterns provided by the original Hadamard basis.

Since LED responses are non-linear and differ from band to band, multiplexed illumination is most effective when the emitting LEDs are each of the same type. Therefore, when different LEDs are used for multi-spectral BRDF measurements, they need to be multiplexed separately for each emitted bandwidth. (There is no restriction when different LEDs are used as detectors.)

As stated above, LEDs emit light at precise bandwidths and have a natural discriminative spectral response. Accordingly, LEDs can be used for active or passive multi-spectral BRDF acquisition. One option is to use multi-band LEDs, which would enable emittance and measurement of different colors from the same location. Multi-band LEDs, however, are currently limited to three bands, and do not produce the same beam pattern for all bands, currently making them difficult to use.

In one implementation, an exemplary system dithers multiple LEDs with multiple wavelengths, thus obtaining multi-spectral BRDF measurement and increasing the spectral resolution of the device. Because an LED with a given wavelength can sense all LEDs with shorter or equal wavelength, using reciprocity, and rotational symmetry of LEDs positions (when the hemisphere or the sample is rotated), the exemplary system can obtain measurement for multiple LED wavelengths and multiple LED positions.

Figure 18:
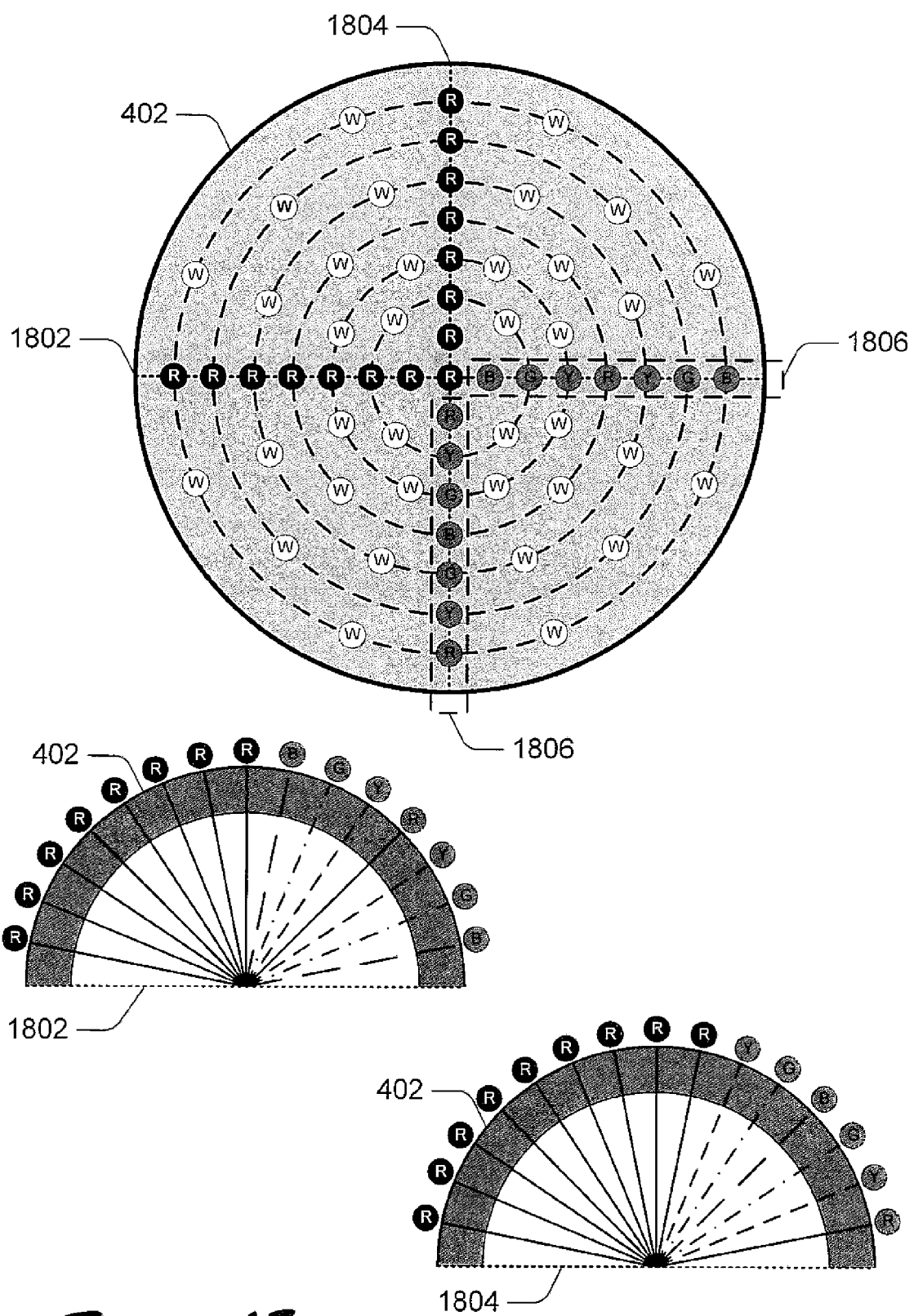
FIG. 18 is a schematic diagram of an exemplary LED arrangement in a photodiode-based BRDF measurement device for multispectral measurement.

FIG. 18 shows a schematic view of an exemplary LED arrangement for multispectral measurement. The hemisphere has two main axes 1802 and 1804 where the LEDs are most dense. The colored LEDs 1806 are spread along one half of each axis. The LEDs on the remaining halves of the axes (shown as black circles labeled with an "R") and the rest of the LEDs (shown as circles labeled with a "W") can either be red or white. (Red LEDs can sense all the other ones, and all the LEDs can sense the white ones.) BRDF reciprocity provides the reverse direction for the same wavelength.

The number of LED units used may be limited by the hemisphere size, thus a larger hemisphere can accommodate more LED units, but will sometimes be less portable. Higher resolution also means a smaller solid angle of collectable light, which reduces the signal-to-noise ratio. For an LED element of 1 cm square, and a hemisphere of radius 10-15 cm the number of LED units that can be implemented are approximately between 500-1400 respectively. To increase resolution, it is possible to take multiple measurements while moving the LED units slightly, for example, if the LED unit size is 1 cm, and four different measurements are taken with displacements of 0.5 cm in x and y directions, then it is possible to compute hi-resolution data of 4 times (2×2) the original resolution. This applies the known technique of "reconstructional super resolution" to BRDF measurement. It is worth noting, however, that there is a difference due to the fact that with each movement, the illumination direction changes as well as the light capture direction. Super-resolution is more applicable to non-isotropic BRDFs than isotropic BRDFs, and it noted that movement of the LED units as described above can lead to inaccuracies when capturing values for non-isotropic BRDFs.

Figure 19:
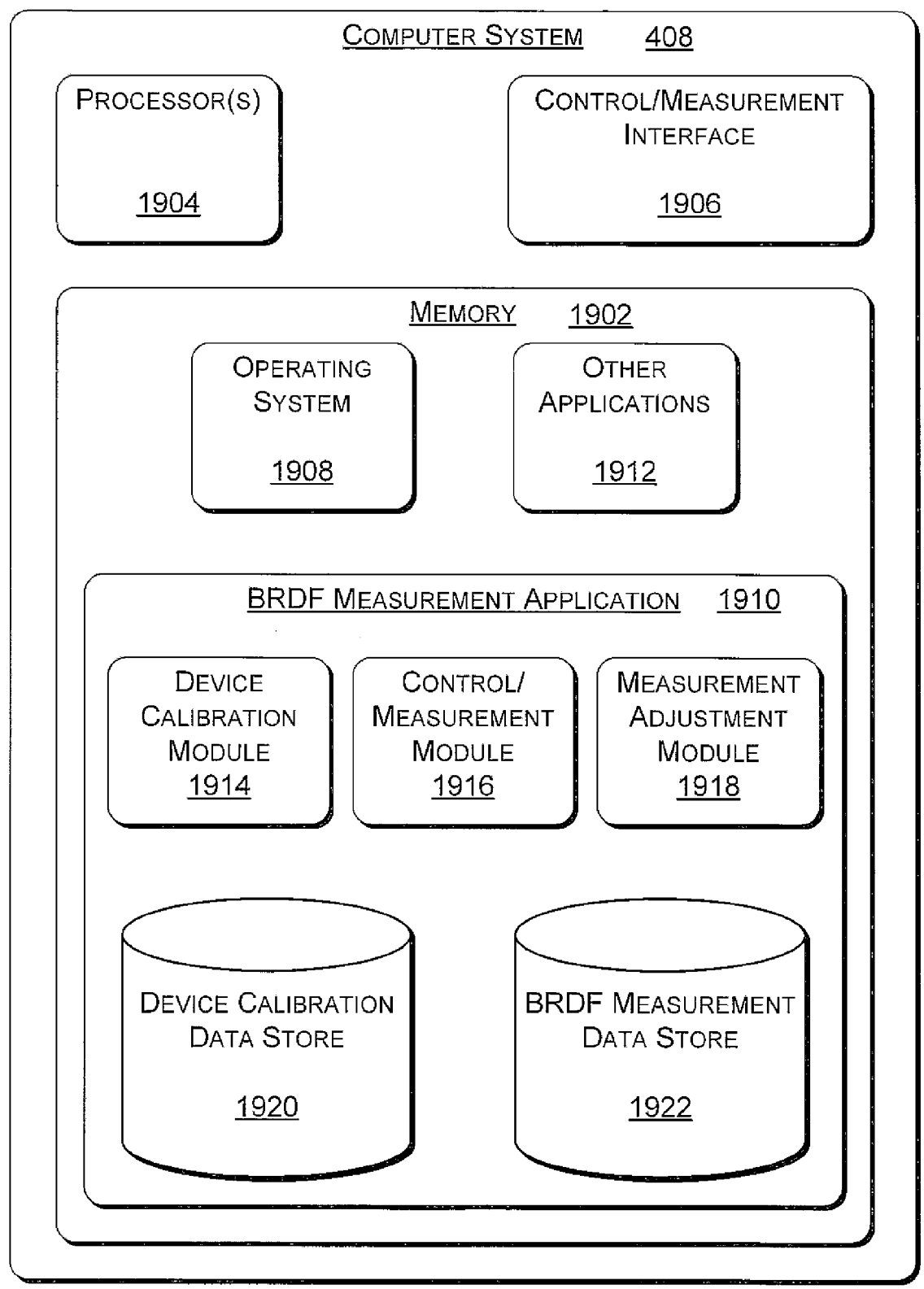
FIG. 19 is a block diagram of a computer system implemented as a component of an exemplary BRDF measurement system.

FIG. 19 is a block diagram of an exemplary computer system 408 implemented as part of BRDF measurement system 400. Exemplary computer system 408 includes a memory 1902 and one or more processors 1904 (e.g., any of microprocessors, controllers, and the like), and control/measurement interface 1906.

The one or more processors 1904 process various computer executable instructions to control the operation of computer system 408 and to communicate with other electronic and computing devices.

An operating system 1908, BRDF measurement application 1910, and any number of other applications 1912 are stored in memory 1902 and executed on processor 1904. Exemplary BRDF measurement application 1910 includes device calibration module 1914, control/measurement module 1916, measurement adjustment module 1918, device calibration data store 1920, and BRDF measurement data store 1922.

Device calibration module 1914 is configured to obtain various calibration measurements. For example, as described above, such calibration measurements may include any combination of: responses of each LED to a white LED, responses between each emitter/detector pair of LEDs, dark current, response variations between LEDs of the same type, and stray light for each emitter/detector pair of LEDs. In an exemplary implementation, calibration measurements obtained by device calibration module 1914 are stored in device calibration data store 1920.

Control/measurement module 1916 is configured to control the LEDs, and receive measurements from those LEDs. For example, control/measurement module 1916 sends control data from computer system 408 to measurement head 402 via control/measurement interface 1906. The control data directs one or more LEDs to emit light while directing one or more other LEDs to transmit signals of received light back to computer system 408.

Measurement adjustment module 1918 uses data stored in device calibration data store 1920 to adjust the readings received from the detecting LEDs. The adjusted data is then stored in BRDF measurement data store 1922.

Computer system 408 can be implemented in any number of ways using, for example, any combination of personal computers, server computers, client devices, hand-held or laptop devices, microprocessor-based systems, multiprocessor systems, set top boxes, programmable consumer electronics, network PCs, minicomputers, mainframe computers, distributed computing environments that include any of the above systems or devices, and the like.

Computer system 408 includes a variety of computer readable media which can be any media that is accessible by computer system 408 and includes both volatile and non-volatile media, removable and non-removable media. The memory 1902 includes computer-readable media in the form of volatile memory, such as random access memory (RAM), and/or non-volatile memory, such as read only memory (ROM). Although not shown, computer system 408 may also include other removable/non-removable, volatile/non-volatile computer storage media such as a hard disk drive, which reads from and writes to a non-removable, non-volatile magnetic media; a magnetic disk drive, which reads from and writes to a removable, non-volatile magnetic disk; and an optical disk drive, which reads from and/or writes to a removable, non-volatile optical disk such as a CD-ROM, digital versatile disk (DVD), or any other type of optical media. The disk drives and associated computer readable media provide non-volatile storage of computer readable instructions, data structures, program modules, and other data for computer system 408.

Methods for implementing photodiode-based BRDF measurement may be described in the general context of computer executable instructions. Generally, computer executable instructions include routines, programs, objects, components, data structures, procedures, and the like that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

Figure 20:
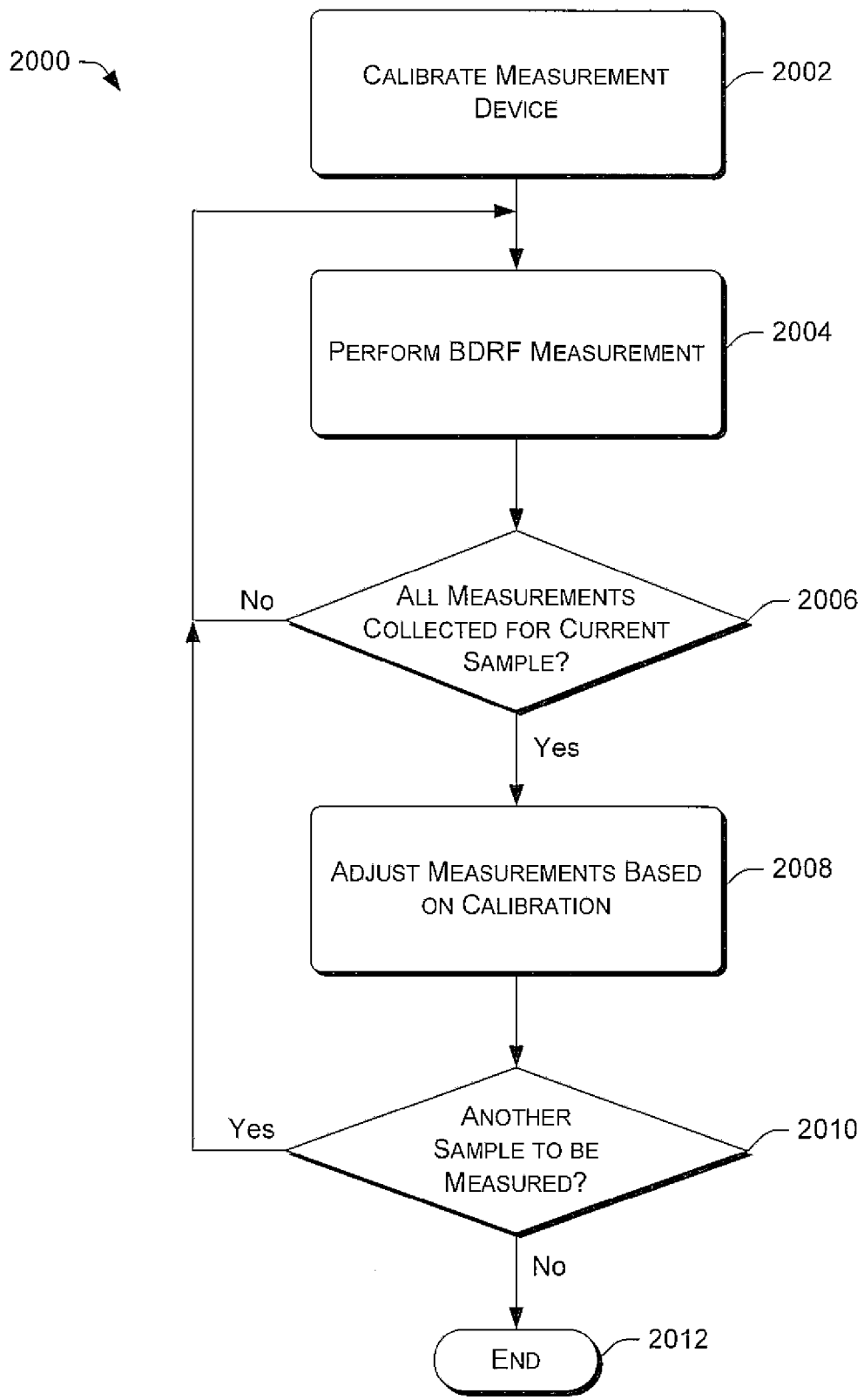
FIG. 20 is a flow diagram of a method for using an exemplary BRDF measurement system.
Figure 21:
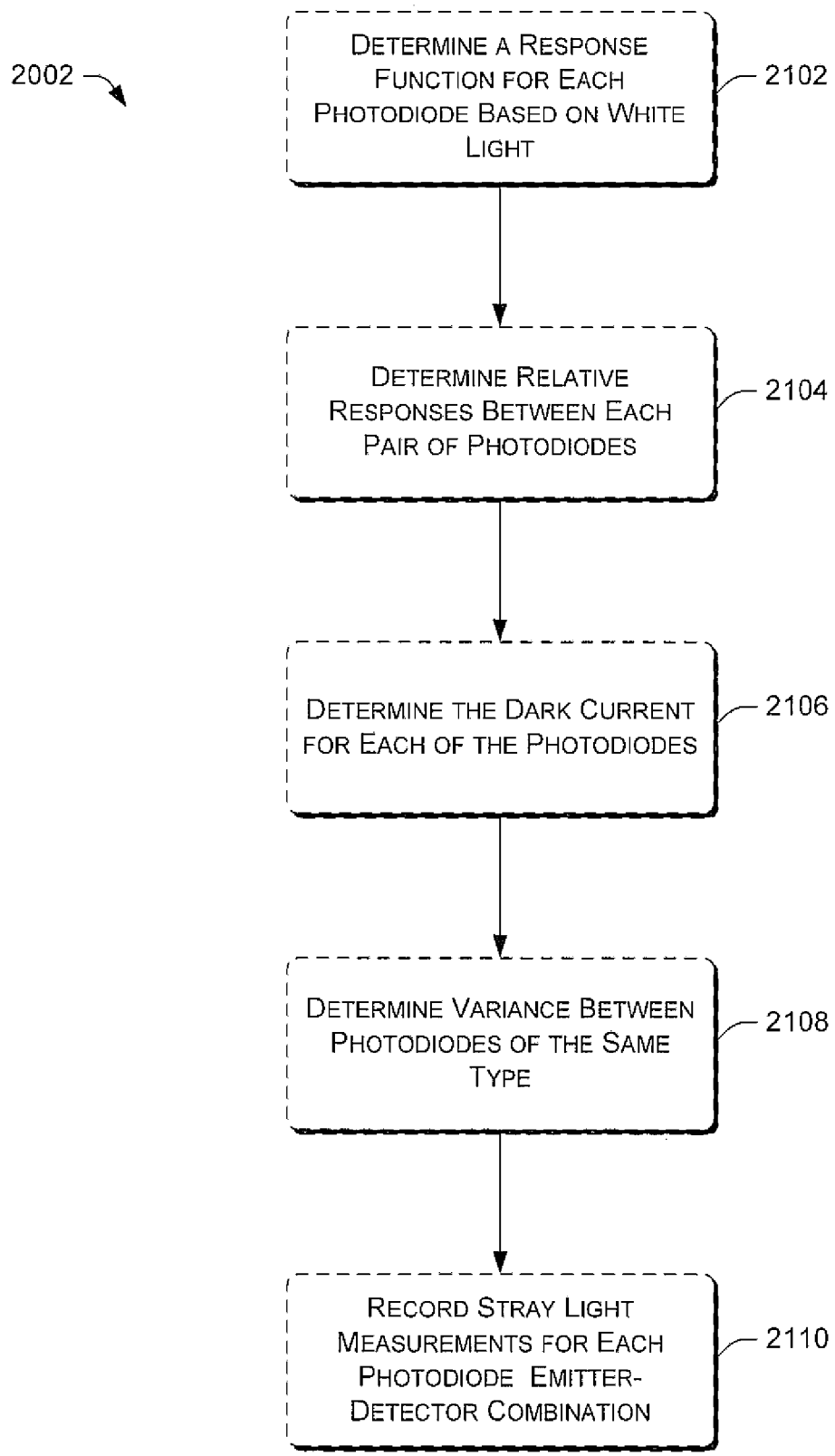
FIG. 21 is a flow diagram of an exemplary method for calibrating a BRDF measurement system.
Figure 22:
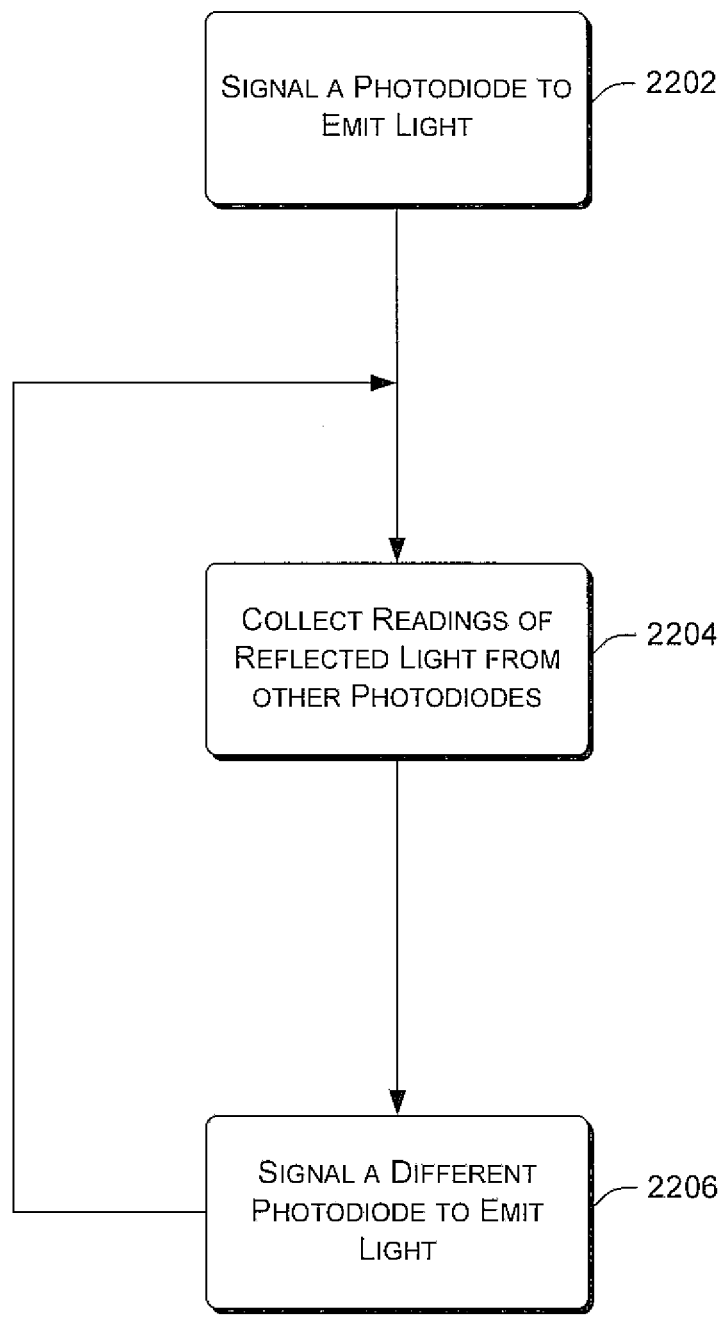
FIG. 22 is a flow diagram of an exemplary method for capturing BRDF measurements.

FIGS. 20-22 illustrate exemplary methods for photodiode-based BRDF measurement. FIGS. 20-22 are specific examples of BRDF measurement, and are not to be construed as limitations. The order in which the method blocks are described is not intended to be construed as a limitation, and any number of the described method blocks can be combined in any order to implement the methods. Furthermore, the methods can be implemented in any suitable hardware, software, firmware, or combination thereof.

FIG. 20 is an example method 2000 of BRDF measurement utilizing an exemplary BRDF measurement system, as described herein. At block 2002, a measurement device is calibrated. For example, device calibration module 1914 gathers calibration data using measurement head 402, and stores the calibration data in device calibration store 1920. In an exemplary implementation, device calibration is performed once for the device, and it is not necessary for the device to be calibrated each time a measurement is taken, or each time a new sample is to be measured.

At block 2004, BRDF measurement is performed. For example, control/measurement module 1916 directs a particular LED unit 404 to emit light, while directing the other LED units to return readings of reflected light.

At block 2006, a determination is made regarding whether or not all of the measurements have been collected for the current sample. If additional measurements remain to be collected (the "No" branch from block 2006), then processing continues as described above at block 2004.

After all measurements have been collected for the current sample (the "Yes" branch from block 2006), at block 2008, the collected measurement values are adjusted based on calibration data. For example, measurement adjustment module 1918 processes the measurements received from the LEDs based on the device calibration data stored in device calibration data store 1920. The processed measurements are then stored in BRDF measurement data store 1922 as BRDF values.

At block 2010, a determination is made regarding whether or not another sample is to be measured. If another sample is to be measured (the "Yes" branch from block 2010), then processing continues as described above at block 2004—but for a new sample. If no additional sample is to be measured, then processing terminates at block 2012.

FIG. 21 is an example method 2002 for BRDF measurement device calibration, as described herein. FIG. 21 illustrates various exemplary processes that may be performed as part of device calibration. It is recognized that any combination of one or more of the illustrated processes may be performed in various implementations.

At block 2102, a response function is determined for each photodiode based on white light. For example, a white LED is placed inside an integrating sphere as a source, and each particular LED (blue, green, yellow, or red) is placed inside the integrating sphere as a detector. Using a regulated power supply, different current levels are driven through the white LED. The voltage of the detector LED is measured for each source current, giving the detector's response function.

At block 2104, relative responses between each pair of photodiodes are determined. For example, a particular LED is placed inside an integrating sphere as a source, and another particular LED is placed inside the integrating sphere as a detector. Using a regulated power supply, different current levels are driven through the emitting LED. The voltage of the detector LED is measured for each source current, giving the detector's response to that particular emitting LED.

At block 2106, a dark current value is determined for each of the photodiodes. For example, several measurements from a particular LED in complete darkness are averaged. The average value is then converted to irradiance space using the inverse response function of the particular LED.

At block 2108, variance between photodiodes of the same type is determined. For example, light emitted from a white LED is diffused using a small spherical diffuser so that the LED provides a nearly isotropic light source over the top hemisphere of the diffuser. Measurements from each of the LEDs installed as detectors are then recorded, and variations between LEDs of the same color are measured and recorded.

At block 2110, stray light measurements for each photodiode emitter/detector combination are recorded. For example, a light trap is placed at the material sample location and signals are measured and recorded for each LED emitter-detector combination.

FIG. 22 is an example method 2004 for performing BRDF measurement, as described herein. At block 2202, a particular photodiode (or combination of photodiodes) is signaled to emit light. For example, control/measurement module 1916 sends a signal to LED unit 404(1) to emit light.

At block 2204, readings of reflected light are collected from other photodiodes. For example, control/measurement module receives readings from each of the other LEDs 404(2), 404(3), 404(4), 404(n).

At block 2206, a different photodiode (or combination of photodiodes) is signaled to emit light. For example, control/measurement module 1916 directs LED 404(2) to emit light.

Processing then continues at block 2204 until recordings have been gathered with each different photodiode acting as an emitter.

Although embodiments of photodiode-based BRDF measurement have been described in language specific to structural features and/or methods, it is to be understood that the subject of the appended claims is not necessarily limited to the specific features or methods described. Rather, the specific features and methods are disclosed as exemplary implementations of photodiode-based BRDF measurement.

What is claimed is:

1. A photodiode-based bi-directional reflectance distribution function (BRDF) measurement system comprising:
   a plurality of photodiode units, wherein each one of the plurality of photodiode units acts, at any particular time, as either a light emitter or a light detector;
   a control module configured to:
      signal one or more of the photodiode units to emit light; and
      while the one or more of the photodiode units are emitting light, receive from one or more others of the photodiode units, readings of light that has impinged on a surface being measured; and
   an adjustment module to convert the readings to BRDF data.

2. The BRDF measurement system as recited in claim 1, wherein the plurality of photodiode units comprise a plurality of light emitting diodes (LEDs) positioned around a location of a surface to be measured via the BRDF measurement system.

3. The BRDF measurement system as recited in claim 1, wherein the plurality of photodiode units are positioned according to a hemisphere around a location of a surface to be measured via the BRDF measurement system.

4. The BRDF measurement system as recited in claim 1, further comprising a camera to capture texture changes with respect to changes of illumination direction to provide a texture map.

5. The BRDF measurement system as recited in claim 4, wherein the camera collects normal vectors of a surface for analysis using a photometric stereo method.

6. The BRDF measurement system as recited in claim 1, wherein:
   each of the plurality of photodiode units comprises:
      a light emitting diode (LED); and
      a lens for controlling light generated by the LED.

7. The BRDF measurement system as recited in claim 6, wherein the LEDs use multiple wavelengths to obtain multi-spectral BRDF measurement.

8. The BRDF measurement system as recited in claim 1, further comprising multiplexing logic to signal multiple ones of the plurality of photodiode units to emit light simultaneously, and de-multiplexing logic to obtain reflectance data from multiple other ones of the plurality of photodiode units receiving reflected light.

9. A photodiode-based bi-directional reflectance distribution function (BRDF) measurement system comprising:
   a plurality of photodiode units, wherein:
      each one of the plurality of photodiode units acts, at any particular time, as either a light emitter or a light detector;
      each of the plurality of photodiode units comprises:
         a light emitting diode (LED); and
         a lens for controlling light generated by the LED; and
      a mount having a plurality of wells, wherein:
         each LED is fixed at one end of a respective well in the mount; and
         a lens for controlling light generated by the LED is fixed at the other end of the respective well.

10. The BRDF measurement system as recited in claim 9, wherein the well is dark in color to absorb stray light emitted from the LED.

11. The BRDF measurement system as recited in claim 9, wherein the mount comprises a heat-sinking material to dissipate heat generated by the plurality of LEDs.

12. The BRDF measurement system as recited in claim 9, wherein the mount is hemispherical.

13. The BRDF measurement system as recited in claim 9, wherein the lens comprises a Fresnel lens.

14. The BRDF measurement system as recited in claim 9, further comprising a movement controller to move the mount in fixed distances to obtain multiple measurements to increase resolution.

15. The BRDF measurement system as recited in claim 9, wherein the LEDs use multiple wavelengths to obtain multi-spectral BRDF measurement.

16. A method for measuring bi-directional reflectance distribution function (BRDF) values comprising:
   arranging a plurality of photodiode units approximately symmetrically around a surface;
   signaling a first of the photodiode units to emit light while simultaneously signaling a second of the photodiode units to detect light reflected from the surface;
   recording from the second of the photodiode units, a measurement of light reflected from the surface;
   subsequently signaling the second of the photodiode units to emit light while simultaneously signaling the first of the photodiode units to detect light reflected from the surface;
   recording from the first of the photodiode units, a measurement of light reflected from the surface; and
   processing the measurements that are recorded to determine BRDF values.

17. The method as recited in claim 16, wherein the plurality of photodiode units comprises a plurality of light emitting diodes (LEDs), the method further comprising:
   determining a response function for each LED, wherein the response function for a particular LED represents the particular LED's response to detected light of varying intensity,
   wherein the processing the measurements that are recorded to determine BRDF values comprises processing each measurement based on the response function for the specific LED from which the measurement was received.

18. The method as recited in claim 16, wherein the plurality of photodiode units comprises a plurality of light emitting diodes (LEDs), the method further comprising:
   using reciprocity and rotational symmetry of LED positions to obtain measurement for multiple LED wavelengths and multiple LED positions.

* * * * *